(12) United States Patent
Flohr et al.

(10) Patent No.: US 8,946,427 B2
(45) Date of Patent: Feb. 3, 2015

(54) TRIAZOLOPYRIDINE COMPOUNDS

(71) Applicant: Hoffmann-La Roche Inc., Nutley, NJ (US)

(72) Inventors: Alexander Flohr, Loerrach (DE); Katrin Groebke Zbinden, Liestal (CH); Matthias Koerner, Grenzach-Wyhlen (DE)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 14/218,275

(22) Filed: Mar. 18, 2014

(65) Prior Publication Data

US 2014/0303141 A1    Oct. 9, 2014

Related U.S. Application Data

(63) Continuation of application No. PCT/EP2012/068203, filed on Sep. 17, 2012.

(30) Foreign Application Priority Data

Sep. 19, 2011    (EP) .................................... 11181752

(51) Int. Cl.
 *C07D 471/04*    (2006.01)
(52) U.S. Cl.
 CPC .................................. *C07D 471/04* (2013.01)
 USPC ....................................................... 546/119

(58) Field of Classification Search
 USPC .......................................................... 546/119
 See application file for complete search history.

(56) References Cited

FOREIGN PATENT DOCUMENTS

WO    2010/059836    *    5/2010

* cited by examiner

*Primary Examiner* — D M Seaman
(74) *Attorney, Agent, or Firm* — Robert C. Hall

(57) ABSTRACT

The invention is concerned with triazolopyridine compounds of formula (I)

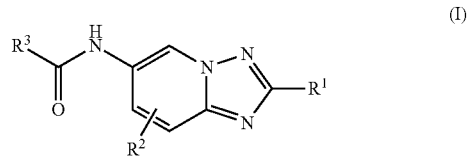

wherein $R^1$, $R^2$ and $R^3$ are as defined in the description and in the claims, as well as physiologically acceptable salts thereof. These compounds inhibit PDE10A and can be used as medicaments.

9 Claims, No Drawings

TRIAZOLOPYRIDINE COMPOUNDS

CROSS REFERENCE TO RELATED APPLICATIONS

This application is a Continuation of International Application No. PCT/EP2012/068203 filed on Sep. 17, 2012, which is entitled to the priority of EP Application No. 11181752.4 filed on Sep. 19, 2011, the disclosures of which are incorporated herein by reference in their entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 28:325-33, 2000). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 5(4): 507-518, 2001; Nakazato A and Okuyama S, et al., Exp. Opin. Ther. Patents, 10(1): 75-98, 2000). This pharmacological approach, besides ameliorating positive symptoms in schizophrenic patients, poorly addresses negative and cognitive symptoms which are the best predictors of functional outcome (Sharma T., Br. J. Psychiatry, 174 (suppl. 28): 44-51, 1999). In addition, current antipsychotic treatment is associated with adverse effects like weight gain, extrapyramidal symptoms or effects on glucose and lipid metabolism, related to their unspecific pharmacology.

In conclusion there is still a need for developing new antipsychotics with improved efficacy and safety profile. A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly, in healthy volunteers PCP-induced psychotomimetic action incorporates positive and negative symptoms as well as cognitive dysfunction, thus closely resembling schizophrenia in patients (Javitt D C et al., Biol. Psychiatry, 45: 668-679, 1999).

Cyclic nucleotides cyclic adenosine monophosphate (cAMP) and cyclic guanosine monophosphate (cGMP) are ubiquitous second messengers responsible for mediating the biological response of a variety of extracellular signals, including neurotransmitters, light and hormones. cAMP and cGMP regulate a variety of intracellular processes particularly in neurons of the central nervous system by activating cAMP- and cGMP-dependent kinases which then phosphorylate proteins involved in the regulation of synaptic transmission, neuronal differentiation and survival.

A crucial mechanism for controlling intracellular cyclic nucleotide levels and therefore cyclic nucleotide signaling is via hydrolysis of the 3',5'-phosphodiester bond by phosphodiesterases. Phosphodiesterases (PDEs) are a family of widely expressed enzymes encoded by 21 different genes in humans, with each gene encoding several splice variants (Beavo, J., Physiol. Rev. 1995, 75, 725-748; Conti, M., Jin, S. L., Prog. Nucleic Acid Res. Mol. Biol. 1999, 63, 1-38; Soderling, S. H., Beavo, J. A., Curr. Opin. Cell Biol. 2000, 12, 174-179, Manallack, D. T. et al. J. Med. Chem. 2005, 48 (10), 3449-3462).

The PDE families differ in their substrate specificy for the cyclic nucleotides, their mechanism of regulation and their sensitivity to inhibitors. Moreover, they are differentially localized in the organism, among the cells of an organ and even within the cells. These differences lead to a differentiated involvement of the PDE families in the various physiological functions.

PDE10A is a dual substrate PDE encoded by a single gene as reported in 1999 by three separate research groups (Fujishige K., et al., Eur J Biochem (1999) 266(3):1118-1127, Soderling S. H., et al., Proc Natl Acad Sci USA (1999) 96(12):7071-7076, Loughney K., et al., Gene (1999) 234(1): 109-117). PDE10A is unique from other members of the multigene family with respect to amino acid sequence (779 aa), tissue-specific pattern of expression, affinity for cAMP and cGMP and the effect on PDE activity by specific and general inhibitors.

PDE10A has one of the most restricted distribution of any PDE family being primarily expressed in the brain particularly in the nucleus accumbens and the caudate putamen. Additionally thalamus, olfactory bulb, hippocampus and frontal cortex show moderate levels of PDE10A expression. All these brain areas have been suggested to be involved in the pathophysiology of schizophrenia and psychosis, suggesting a central role of PDE10A in this devastating mental illness. Outside the central nervous system PDE10A transcript expression is also observed in peripheral tissues like thyroid gland, pituitary gland, insulin secreting pancreatic cells and testes (Fujishige, K. et al., J. Biol. Chem. 1999, 274, 18438-18445, Sweet, L. (2005) WO 2005/012485). On the other hand expression of PDE10A protein has been observed only in enteric ganglia, in testis and epididymal sperm (Coskran T. M, et al., J. Histochem. Cytochem. 2006, 54 (11), 1205-1213).

In the striatum both mRNA and protein are expressed only in the GABA (-aminobutyric acid)-containing medium spiny projection neurons making it an intriguing target for the treatment of diseases of the central nervous system (Fujishige, K. et al., Eur. J. Biochem. 1999, 266, 1118-1127; Seeger, T. F. et al., Brain Res. 2003, 985, 113-126). The striatal medium spiny neurons are the principal input site and first site for information integration in the basal ganglia circuit of the mammalian brain. The basal ganglia are a series of interconnected subcortical nuclei that integrate widespread cortical input with dopaminergic signaling to plan and execute relevant motor and cognitive patterns while suppressing unwanted or irrelevant patterns (Graybiel, A. M. Curr. Biol. 2000, 10, R509-R511 (2000).

Papaverine, a relatively specific PDE10A inhibitor, and PDE10A-knockout mice have been used to explore the physiology of this enzyme and the possible therapeutic utility of PDE10A inhibition Inhibition of this enzyme pharmacologically or through gene disruption causes a reduction in activity and a reduced response to psychomotor stimulants Inhibition also reduces the conditioned avoidance response, a behavioural response that is predictive of clinical antipsychotic activity (Siuciak, J. A.; et al., Neuropharmacology 2006, 51 (2), 386-396; Siuciak, J. A.; et al., Neuropharmacology 2006, 51 (2), 374-385).

In addition PDE10A inhibition bears the potential to improve the negative and cognitive symptoms associated to schizophrenia. Indeed papaverine have been shown to attenuate the deficits in the extra-dimensional shift learning induced in rats by sub-chronic treatment with PCP, an animal paradigm of NMDA receptor hypofunction (Rodefer, J, S., et al., Eur. J. Neuroscience 2005, 2,: 1070-1076). In addition increased social interaction in PDE10A2-deficient mice have been observed (Sano, H. J. Neurochem. 2008, 105, 546-556).

Diseases that can be treated with PDE10A inhibitors include, but are not limited to, diseases thought to be mediated in part by dysfunction of the basal ganglia, of other parts of the central nervous system and of other PDE10A expressing tissues. In particular, diseases can be treated, where inhibition of PDE10A can have therapeutic effects.

These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

The compounds of the present invention are also suitable for the treatment of diabetes and related disorders such as obesity by regulating the cAMP signaling system.

PDE10A inhibitors might also be useful in preventing neurons from undergoing apoptosis by raising cAMP and cGMP levels and, thus, might possess anti-inflammatory properties. Neurodegenerative disorders treatable with PDE10A inhibitors include, but are not limited to, as Alzheimer's disease, Huntington's disease, Parkinson's disease, multiple sclerosis, stroke or spinal cord injury.

The growth of cancer cells is inhibited by cAMP and cGMP. Thus by raising cAMP and cGMP, PDE10A inhibitors can also be used for the treatment of different solid tumors and hematological malignancies such as renal cell carcinoma or breast cancer.

SUMMARY OF THE INVENTION

The present invention relates to novel compounds of formula (I)

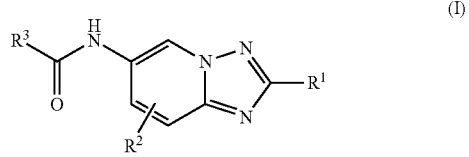

(I)

wherein $R^1$ is aryl, heteroaryl or $NR^4R^5$, wherein said aryl and said heteroaryl can be substituted by 1 to 3 substituents independently selected from the group consisting of hydroxyl, halogen, $C_1$-$C_7$ alkyl, $C_1$-$C_7$ alkoxy and $C_1$-$C_7$ haloalkyl;

$R^2$ is hydrogen, halogen or $C_1$-$C_7$ alkyl;

$R^3$ is aryl or heteroaryl, wherein said aryl and said heteroaryl can be substituted by 1 to 3 substituents independently selected from the group consisting of $C_1$-$C_7$ alkyl, hydroxyl, halogen, —C(O)—$NR^6R^7$ and —C(O)—O—$R^8$;

$R^4$ and $R^5$ are independently $C_1$-$C_7$ alkyl, $C_3$-$C_8$ cycloalkyl, together with the nitrogen atom to which they are attached, form a heterocycloalkyl which can be substituted by 1 to 3 substituents independently selected from the group consisting of hydroxyl, halogen, $C_1$-$C_7$ alkyl, $C_1$-$C_7$ alkoxy and $C_1$-$C_7$ haloalkyl;

$R^6$ and $R^7$, are independently $C_1$-$C_7$ alkyl, $C_3$-$C_8$ cycloalkyl, together with the nitrogen atom to which they are attached, form a heterocycloalkyl which can be substituted by 1 to 3 substituents independently selected from the group consisting of hydroxyl, halogen, $C_1$-$C_7$ alkyl, $C_1$-$C_7$ alkoxy and $C_1$-$C_7$ haloalkyl;

$R^8$ is hydrogen, $C_1$-$C_7$ alkyl, cycloalkyl;

or a pharmaceutically acceptable salt thereof.

Further, the invention is concerned with a process for the manufacture of the above compounds, pharmaceutical preparations which contain such compounds as well as the use of these compounds for the production of pharmaceutical preparations.

DETAILED DESCRIPTION OF THE INVENTION

Unless otherwise indicated, the following definitions are set forth to illustrate and define the meaning and scope of the various terms used to describe the invention herein.

It must be noted that, as used in the specification and the claims, the singular forms "a", "an" and "the" include plural referents unless the context clearly dictates otherwise.

When indicating the number of substituents, the term "one or more" means from one substituent to the highest possible number of substitution, i.e. replacement of one hydrogen up to replacement of all hydrogens by substituents.

The term "optional" or "optionally" denotes that a subsequently described event or circumstance may but need not occur, and that the description includes instances where the event or circumstance occurs and instances in which it does not.

The term "halogen" refers to fluorine, chlorine, bromine and iodine, more specifically fluorine, chlorine and bromine.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "alkoxy" denotes a group of the formula —O—R', wherein R' is an alkyl group. Examples of alkoxy moieties include methoxy, ethoxy, isopropoxy, and tert-butoxy.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms.

The term "aryl" denotes a monovalent aromatic carbocyclic mono- or bicyclic ring system comprising 6 to 10 carbon ring atoms. Examples of aryl moieties include phenyl and naphthyl The term "amino" refers to a monovalent group that has a nitrogen atom with two hydrogen atoms (represented by —NH2).

The term "oxo" when referring to substituents on heterocycloalkyl means that an oxygen atom is attached to the heterocycloalkyl ring. Thereby, the "oxo" may either replace two hydrogen atoms on a carbon atom, or it may simply be attached to sulfur, so that the sulfur exists in oxidized form, i.e. bearing one or two oxygens.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

Compounds of formula (I) can form pharmaceutically acceptable salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) which comprise an acidic group, such as e.g. a COOH group, can further form salts with bases. Examples of such salts are alkaline, earth-alkaline and ammonium salts such as e.g. Na—, K—, Ca— and trimethylammonium salt. The term "pharmaceutically acceptable salts" also refers to such salts. Particular salts are those obtained by the addition of an acid.

The term "pharmaceutically acceptable esters" embraces derivatives of the compounds of formula (I), in which a carboxy group has been converted to an ester. Lower alkyl, lower hydroxyalkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. Particular esters are methyl, ethyl, propyl, butyl and benzyl esters. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

It will be appreciated that the compounds of general formula (I) in this invention may be derivatised at functional groups to provide derivatives which are capable of conversion back to the parent compound in vivo.

The present invention relates to novel compounds of formula (I)

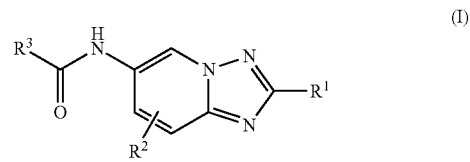

wherein $R^1$ is aryl, heteroaryl or $NR^4R^5$, wherein said aryl and said heteroaryl can be substituted by 1 to 3 substituents independently selected from the group consisting of hydroxyl, halogen, $C_1$-$C_7$ alkyl, $C_1$-$C_7$ alkoxy and $C_1$-$C_7$ haloalkyl;

$R^2$ is hydrogen, halogen or $C_1$-$C_7$ alkyl;

$R^3$ is aryl or heteroaryl, wherein said aryl and said heteroaryl can be substituted by 1 to 3 substituents independently selected from the group consisting of $C_1$-$C_7$ alkyl, hydroxyl, halogen, —C(O)—$NR^6R^7$ and —C(O)—O—$R^8$;

$R^4$ and $R^5$ are independently $C_1$-$C_7$ alkyl, $C_3$-$C_8$ cycloalkyl, together with the nitrogen atom to which they are attached, form a heterocycloalkyl which can be substituted by 1 to 3 substituents independently selected from the group consisting of hydroxyl, halogen, $C_1$-$C_7$ alkyl, $C_1$-$C_7$ alkoxy and $C_1$-$C_7$ haloalkyl;

$R^6$ and $R^7$, are independently $C_1$-$C_7$ alkyl, cycloalkyl, together with the nitrogen atom to which they are attached, form a heterocycloalkyl which can be substituted by 1 to 3 substituents independently selected from the group consisting of hydroxyl, halogen, $C_1$-$C_7$ alkyl, $C_1$-$C_7$ alkoxy and $C_1$-$C_7$ haloalkyl;

$R^8$ is hydrogen, $C_1$-$C_7$ alkyl, cycloalkyl;

or a pharmaceutically acceptable salt thereof.

In a particular embodiment the invention relates to compounds of formula (I), wherein $R^1$ is phenyl, pyridinyl, thiazolyl or $NR^4R^5$, wherein $R^4$ and $R^5$ are independently selected from $C_1$-$C_3$ alkyl, $R^4$ and $R^5$ together with the nitrogen atom to which they are attached, form a pyrrolidinyl or morpholinyl ring.

In a further particular embodiment the invention relates to compounds of formula (I), wherein $R^2$ is hydrogen.

In yet another embodiment the invention relates to compounds of formula (I), wherein $R^3$ is:

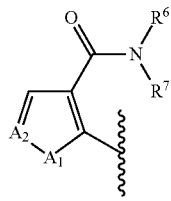

wherein:
$A_1$ is $NR^9$,
$A_2$ is $NR^{9'}$,
$R^6$ and $R^7$ are independently selected from $C_1$-$C_3$ alkyl, $C_3$-$C_8$ cycloalkyl, both optionally substituted by 1 to 3 substituents independently selected from halogen, $C_1$-$C_3$ alkyl, $C_1$-$C_3$ alkoxy and $C_1$-$C_3$ haloalkyl;
$R^6$ and $R^7$ together with the nitrogen atom to which they are attached form a heterocycloalkyl of 4 to 7 ring atoms, comprising 1 or 2 ring heteroatoms selected from N and O, the heterocycloalkyl optionally substituted by 1 to 3 substituents independently selected from halogen, $C_1$-$C_3$ alkyl, $C_1$-$C_3$ alkoxy and $C_1$-$C_3$ haloalkyl,
$R^9$ and $R^{9'}$ are independently selected from hydrogen, $C_1$-$C_3$ alkyl, $C_1$-$C_3$ alkoxy and $C_1$-$C_3$ haloalkyl.

Another particular embodiment relates to compounds of formula (I), wherein:
$R^6$ and $R^7$ are independently selected from $C_1$-$C_3$ alkyl, $C_3$-$C_8$ cycloalkyl,
$R^6$ and $R^7$ together with the nitrogen atom to which they are attached form azetidinyl, pyrrolidinyl and morpholinyl which are optionally substituted by 1 to 3 substituents independently selected from the group consisting of halogen, $C_1$-$C_3$ alkyl, $C_1$-$C_3$ alkoxy and $C_1$-$C_3$ haloalkyl.
$R^9$ is selected from $C_1$-$C_3$ alkyl, $C_1$-$C_3$ alkoxy and $C_1$-$C_3$ haloalkyl, preferably $C_1$-$C_3$ alkyl,
$R^{9'}$ is selected from hydrogen and $C_1$-$C_3$ alkyl, preferably hydrogen.

Particular compounds of formula (I) are selected from the group consisting of:
2-Methyl-4-(pyrrolidine-1-carbonyl)-2H-pyrazole-3-carboxylic acid (2-phenyl-[1,2,4]triazolo[1,5-a]pyridin-6-yl)-amide
1-Methyl-5-(2-phenyl-[1,2,4]triazolo[1,5-a]pyridin-6-ylcarbamoyl)-1H-pyrazole-4-carboxylic acid
4-(Azetidine-1-carbonyl)-2-methyl-2H-pyrazole-3-carboxylic acid (2-phenyl-[1,2,4]triazolo[1,5-a]pyridin-6-yl)-amide
4-(Azetidine-1-carbonyl)-1-methyl-N-(2-(thiazol-4-yl)-[1,2,4]triazolo[1,5-a]pyridin-6-yl)-1H-pyrazole-5-carboxamide
1-Methyl-4-(morpholine-4-carbonyl)-N-(2-phenyl-[1,2,4]triazolo[1,5-a]pyridin-6-yl)-1H-pyrazole-5-carboxamide
4-(3-Fluoro-azetidine-1-carbonyl)-2-methyl-2H-pyrazole-3-carboxylic acid (2-phenyl-[1,2,4]triazolo[1,5-a]pyridin-6-yl)-amide
2-Methyl-2H-pyrazole-3,4-dicarboxylic acid 4-(ethyl-methyl-amide) 3-[(2-phenyl-[1,2,4]triazolo[1,5-a]pyridin-6-yl)-amide]
2-Methyl-2H-pyrazole-3,4-dicarboxylic acid 4-(cyclopropyl-methyl-amide) 3-[(2-phenyl-[1,2,4]triazolo[1,5-a]pyridin-6-yl)-amide]
2-Methyl-4-(morpholine-4-carbonyl)-2H-pyrazole-3-carboxylic acid (2-pyridin-3-yl-[1,2,4]triazolo[1,5-a]pyridin-6-yl)-amide
4-(Azetidine-1-carbonyl)-1-methyl-N-(2-(pyridin-3-yl)-[1,2,4]triazolo[1,5-a]pyridin-6-yl)-1H-pyrazole-5-carboxamide
N4-Cyclopropyl-N4,1-dimethyl-N5-(2-(pyridin-3-yl)-[1,2,4]triazolo[1,5-a]pyridin-6-yl)-1H-pyrazole-4,5-dicarboxamide
1-Methyl-N-(2-(pyridin-3-yl)-[1,2,4]triazolo[1,5-a]pyridin-6-yl)-4-(pyrrolidine-1-carbonyl)-1H-pyrazole-5-carboxamide
2-Methyl-4-(pyrrolidine-1-carbonyl)-2H-pyrazole-3-carboxylic acid (2-morpholin-4-yl-[1,2,4]triazolo[1,5-a]pyridin-6-yl)-amide
2-Methyl-4-(morpholine-4-carbonyl)-2H-pyrazole-3-carboxylic acid (2-morpholin-4-yl-[1,2,4]triazolo[1,5-a]pyridin-6-yl)-amide
2-Methyl-4-(azetidine-4-carbonyl)-2H-pyrazole-3-carboxylic acid (2-morpholin-4-yl-[1,2,4]triazolo[1,5-a]pyridin-6-yl)-amide
2-Methyl-2H-pyrazole-3,4-dicarboxylic acid 4-(ethyl-methyl-amide) 3-[(2-morpholin-4-yl-[1,2,4]triazolo[1,5-a]pyridin-6-yl)-amide]
4-(3-Fluoro-azetidine-1-carbonyl)-2-methyl-2H-pyrazole-3-carboxylic acid (2-morpholin-4-yl-[1,2,4]triazolo[1,5-a]pyridin-6-yl)-amide
2-Methyl-2H-pyrazole-3,4-dicarboxylic acid 4-(cyclopropyl-methyl-amide) 3-[(2-morpholin-4-yl-[1,2,4]triazolo[1,5-a]pyridin-6-yl)-amide]
2-Methyl-4-(morpholine-4-carbonyl)-2H-pyrazole-3-carboxylic acid (2-dimethylamino-[1,2,4]triazolo[1,5-a]pyridin-6-yl)-amide
4-(Azetidine-1-carbonyl)-2-methyl-2H-pyrazole-3-carboxylic acid (2-dimethylamino-[1,2,4]triazolo[1,5-a]pyridin-6-yl)-amide
2-Methyl-4-(pyrrolidine-1-carbonyl)-2H-pyrazole-3-carboxylic acid (2-dimethylamino-[1,2,4]triazolo[1,5-a]pyridin-6-yl)-amide
2-Methyl-2H-pyrazole-3,4-dicarboxylic acid 3-[(2-dimethylamino-[1,2,4]triazolo[1,5-a]pyridin-6-yl)-amide]4-(ethyl-methyl-amide)
4-(3-Fluoro-azetidine-1-carbonyl)-2-methyl-2H-pyrazole-3-carboxylic acid (2-dimethylamino-[1,2,4]triazolo[1,5-a]pyridin-6-yl)-amide
2-Methyl-2H-pyrazole-3,4-dicarboxylic acid 4-(cyclopropyl-methyl-amide) 3-[(2-dimethylamino-[1,2,4]triazolo[1,5-a]pyridin-6-yl)-amide]
6-cyclopropyl-3-methoxy-N-(2-phenyl-[1,2,4]triazolo[1,5-a]pyridin-6-yl)pyrazine-2-carboxamide
2-Methyl-4-(morpholine-4-carbonyl)-2H-pyrazole-3-carboxylic acid (2-diethylamino-[1,2,4]triazolo[1,5-a]pyridin-6-yl)-amide
2-Methyl-4-(pyrrolidine-4-carbonyl)-2H-pyrazole-3-carboxylic acid (2-diethylamino-[1,2,4]triazolo[1,5-a]pyridin-6-yl)-amide
2-Methyl-4-(azetitine-4-carbonyl)-2H-pyrazole-3-carboxylic acid (2-diethylamino-[1,2,4]triazolo[1,5-a]pyridin-6-yl)-amide
2-Methyl-2H-pyrazole-3,4-dicarboxylic acid 3-[(2-diethylamino-[1,2,4]triazolo[1,5-a]pyridin-6-yl)-amide]4-(ethyl-methyl-amide)
2-Methyl-2H-pyrazole-3,4-dicarboxylic acid 4-diethylamide 3-[(2-diethylamino-1,2,4]triazolo[1,5-a]pyridin-6-yl)-amide 2-Methyl-2H-pyrazole-3,4-dicarboxylic acid 4-(cyclopropyl-methyl-amide) 3-[(2-diethylamino-[1,2,4]triazolo[1,5-a]pyridin-6-yl)-amide
2-Methyl-4-(morpholine-4-carbonyl)-2H-pyrazole-3-carboxylic acid (2-pyrrolidin-1-yl-[1,2,4]triazolo[1,5-a]pyridin-6-yl)-amide
4-(Azetidine-1-carbonyl)-2-methyl-2H-pyrazole-3-carboxylic acid (2-pyrrolidin-1-yl-[1,2,4]triazolo[1,5-a]pyridin-6-yl)-amide
2-Methyl-4-(pyrrolidine-1-carbonyl)-2H-pyrazole-3-carboxylic acid (2-pyrrolidin-1-yl-[1,2,4]triazolo[1,5-a]pyridin-6-yl)-amide
2-Methyl-2H-pyrazole-3,4-dicarboxylic acid 4-(cyclopropyl-methyl-amide) 3-[(2-pyrrolidin-1-yl-[1,2,4]triazolo[1,5-a]pyridin-6-yl)-amide
2-Methyl-2H-pyrazole-3,4-dicarboxylic acid 4-(ethyl-methyl-amide) 3-[(2-pyrrolidin-1-yl-[1,2,4]triazolo[1,5-a]pyridin-6-yl)-amide
2-Methyl-2H-pyrazole-3,4-dicarboxylic acid 4-diethylamide 3-[(2-pyrrolidin-1-yl-[1,2,4]triazolo[1,5-a]pyridin-6-yl)-amide
2-Methyl-2H-pyrazole-3,4-dicarboxylic acid 4-diethylamide 3-{[2-(3-methoxy-pyrrolidin-1-yl)-[1,2,4]triazolo[1,5-a]pyridin-6-yl]-amide
2-Methyl-4-(morpholine-4-carbonyl)-2H-pyrazole-3-carboxylic acid [2-(3-methoxy-pyrrolidin-1-yl)-[1,2,4]triazolo[1,5-a]pyridin-6-yl]-amide
2-Methyl-2H-pyrazole-3,4-dicarboxylic acid 4-(ethyl-methyl-amide) 3-{[2-(3-methoxy-pyrrolidin-1-yl)-[1,2,4]triazolo[1,5-a]pyridin-6-yl]-amide}
2-Methyl-2H-pyrazole-3,4-dicarboxylic acid 4-(cyclopropyl-methyl-amide) 3-{[2-(3-methoxy-pyrrolidin-1-yl)-[1,2,4]triazolo[1,5-a]pyridin-6-yl]-amide}
2-Methyl-4-(pyrrolidine-1-carbonyl)-2H-pyrazole-3-carboxylic acid [2-(3-methoxy-pyrrolidin-1-yl)-[1,2,4]triazolo[1,5-a]pyridin-6-yl]-amide
4-(Azetidine-1-carbonyl)-2-methyl-2H-pyrazole-3-carboxylic acid [2-(3-methoxy-pyrrolidin-1-yl)-[1,2,4]triazolo[1,5-a]pyridin-6-yl]-amide.

Yet particular compounds of formula (I) are those selected from the group consisting of:
4-(Azetidine-1-carbonyl)-2-methyl-2H-pyrazole-3-carboxylic acid (2-phenyl-[1,2,4]triazolo[1,5-a]pyridin-6-yl)-amide
1-Methyl-4-(morpholine-4-carbonyl)-N-(2-phenyl-[1,2,4]triazolo[1,5-a]pyridin-6-yl)-1H-pyrazole-5-carboxamide
4-(3-Fluoro-azetidine-1-carbonyl)-2-methyl-2H-pyrazole-3-carboxylic acid (2-phenyl-[1,2,4]triazolo[1,5-a]pyridin-6-yl)-amide
2-Methyl-4-(morpholine-4-carbonyl)-2H-pyrazole-3-carboxylic acid (2-pyridin-3-yl-[1,2,4]triazolo[1,5-a]pyridin-6-yl)-amide
2-Methyl-4-(pyrrolidine-1-carbonyl)-2H-pyrazole-3-carboxylic acid (2-morpholin-4-yl-[1,2,4]triazolo[1,5-a]pyridin-6-yl)-amide
2-Methyl-2H-pyrazole-3,4-dicarboxylic acid 4-(cyclopropyl-methyl-amide) 3-[(2-morpholin-4-yl-[1,2,4]triazolo[1,5-a]pyridin-6-yl)-amide]
4-(Azetidine-1-carbonyl)-2-methyl-2H-pyrazole-3-carboxylic acid (2-dimethylamino-[1,2,4]triazolo[1,5-a]pyridin-6-yl)-amide
2-Methyl-2H-pyrazole-3,4-dicarboxylic acid 4-(cyclopropyl-methyl-amide) 3-[(2-dimethylamino-[1,2,4]triazolo[1,5-a]pyridin-6-yl)-amide]

The invention further relates to a process for the manufacture of compounds of formula (I) as defined above, which process comprises:

a) reacting a compound of formula (2)

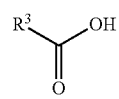

(2)

with
b) a compound of formula (3)

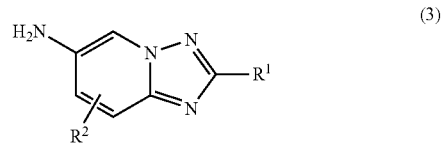

(3)

wherein $R^1$, $R^2$, $R^3$ are as defined above and, if desired, converting the compounds into pharmaceutically acceptable salts thereof.

The reaction described above can be carried out under conditions as described in the description and examples or under conditions well known to the person skilled in the art.

The compounds of formula (2) and (3) can be prepared by methods known in the art or as described below or in analogy thereto.

The present invention also relates to compounds of formula (I) as defined above, when prepared by a process as described above.

Compounds of formula 1 can be prepared from building blocks 2 and 3 according to Scheme 1. The conversion, commonly known as amide coupling, can be achieved in several ways. In one method, the acid 2 is activated with a coupling reagent, such as 2-(1H-benzotriazole-1-yl)-1,1,3,3-tetramethyluronium tetrafluoroborate (TBTU), or propylphosphonic anhydride, and converted by addition of amine 3 to the desired product, 1. In another method, the acid 2 is activated by transformation into an acid chloride, e.g. by reaction with thionyl chloride. The acid chloride is then converted by addition of the amine 3 to the desired product, 1. A base, e.g. diisopropylethylamine (DIPEA), is usually added to bind liberated HCl.

Scheme 1

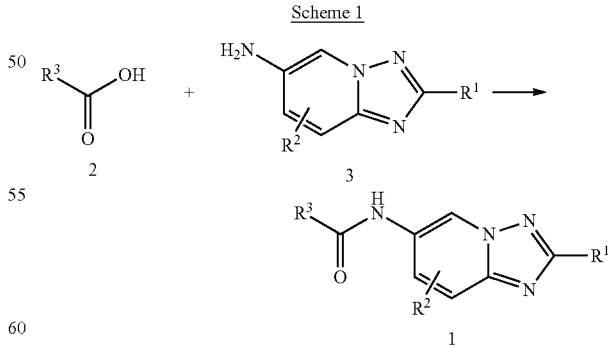

Compounds of formula 3 can be prepared according to Scheme 2: A suitably substituted 2-aminopyridine 4 is reacted with a suitably substituted nitrile 5, 1,10-phenanthroline monohydrate and copper (I) bromide to form compound 6. Compound 6 is then reacted with a compound 7 such as a tert-butyl carbamate to give compound 8. Compound 8 is then converted to amine 3 by methods well known in the art. Compounds 4, 5 and 7 are either commercially available, or can be prepared by methods well known in the art.

thereof, to give a pyrazole 11 (similar to the method of A. Hanzlowsky, B. Jelencic, S. Recnik, J. Svete, A. Golobic, B. Stanovnik J. Heterocyclic Chem. 2003, 40(3), 487-498). Selective mono-saponification of the diester 11 yields, depending on the reaction conditions, compound 2a or its isomer, compound 2b.

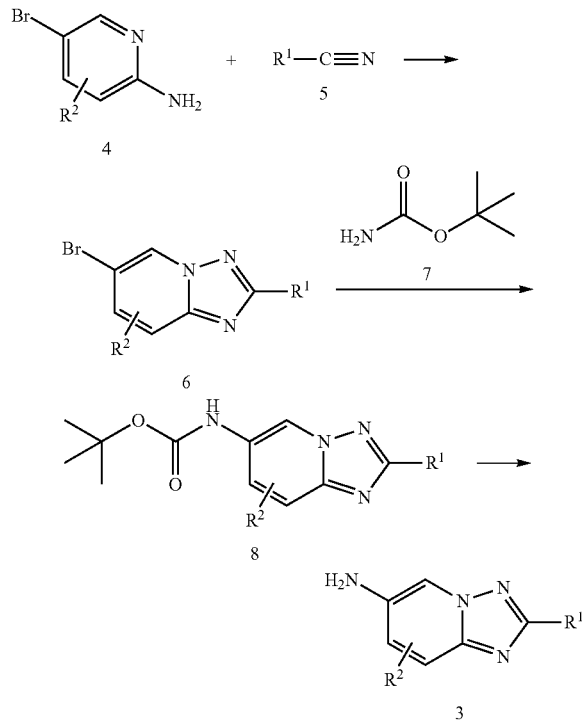

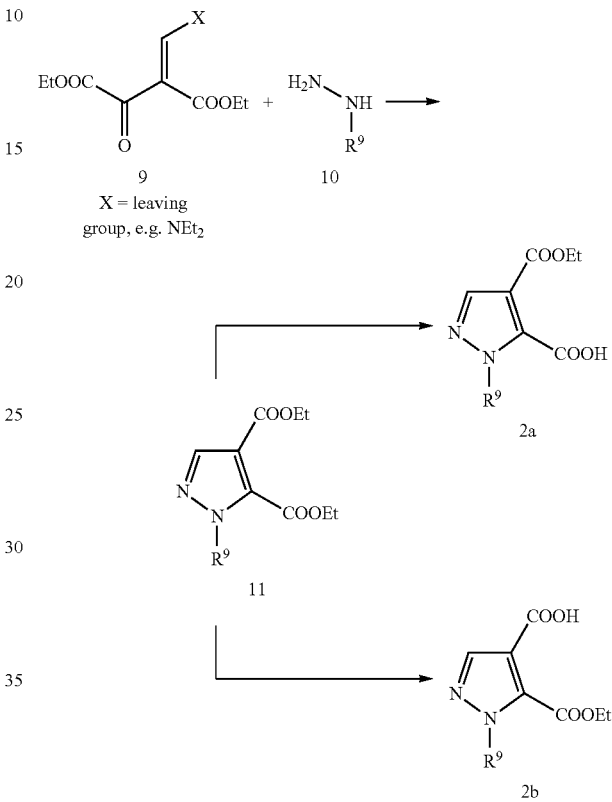

Step 1: 1,10-phenantroline monohydrate, copper (I) bromide

Step 2: Cesium carbonate, tris(dibenzylideneacetone)dipalladium(0), 4,5-bis(diphenylphosphino)-9,9-dimethylxanthene, dioxane Step 3: Hydrochloric acid (5M) in Diethylether Compounds of formula 2, with $R^3$ being a pyrazolyl carboxylic acid derivative, can be prepared according to Scheme 3: Compound 9 is reacted with a hydrazine 10, or a salt Compounds of formula 1, with $R^3$ being a $C_1$-$C_7$ alkoxy-carbonyl-substituted hetero-aromatic ring, can be further transformed according to Scheme 4. For instance, compounds of the general formula 1-COOEt can be saponified by suitable methods, e.g. by reaction with LiOH, to give 1-COOH. Upon activation with a suitable reagent such as TBTU, 1-COOH can be converted with a primary or secondary amine to 1-CONR$_2$. Alternatively, 1-COOEt can be directly converted into 1-CONR$_2$, e.g. by reaction with an amine such as methylamine.

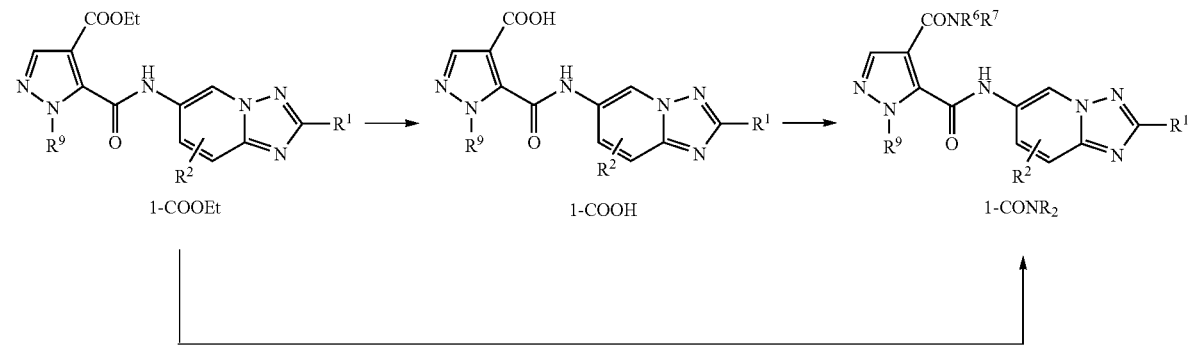

Alternatively, compounds of formula 3, with $R^1$ being $NR^4R^5$, can be prepared according to Scheme 5: A suitably substituted 2-aminopyridine 4 is reacted with ethoxycarbonyl-isothiocyanate 17 to form the thiourea 18, which can be cyclized using hydroxylamine and a suitable base as diisopropylethylamine to a compound of formula 19. This can be converted by methods well known in the art to compound 22 and further to the desired amine of formula 3c. For example, compounds of formula 19 can be treated with a nitrite such as sodium nitrite or alkyl nitrite such as tert.butyl nitrite and a bromide such as copper(II)bromide or benzyl-triethylammonium bromide in a suitable solvent such as acetonitrile or bromoform to form bromide 20. Bromide 20 can then be reacted with an amine of formula 21 in a suitable solvent such as THF or ethanol. A base, e.g. diisopropylethylamine (DIPEA), may be added to the reaction.

2-Amino-5-bromopyrimidine, ethoxycarbonyl-isothiocyanate and hydroxylamine are commercially available; amines 21 are either commercially available, or can be prepared by methods well known in the art.

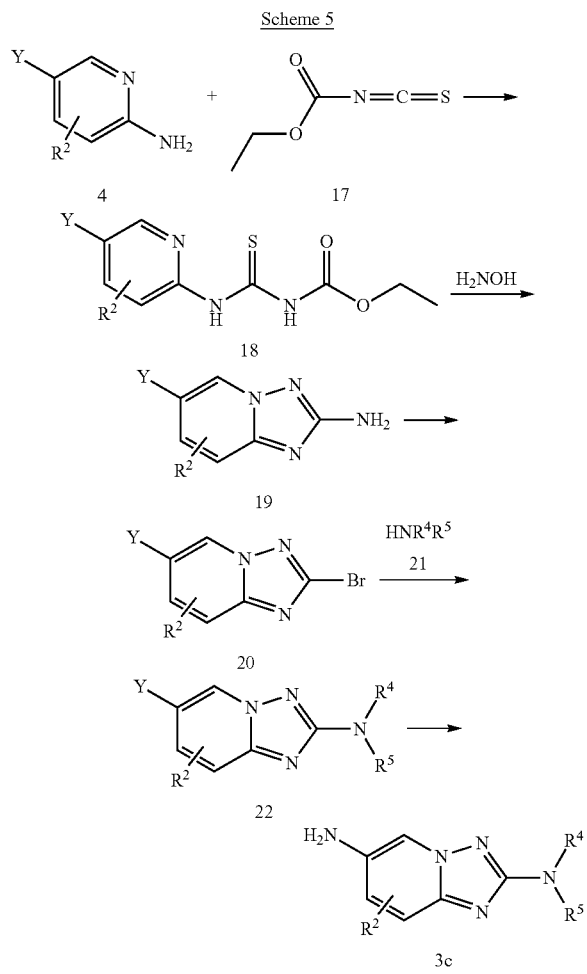

Scheme 5

All reactions are typically performed in a suitable solvent and under an atmosphere of argon or nitrogen.

The corresponding salts with acids can be obtained by standard methods known to the person skilled in the art, e.g. by dissolving the compound of formula (I) in a suitable solvent such as e.g. dioxane or THF and adding an appropriate amount of the corresponding acid. The products can usually be isolated by filtration or by chromatography. The conversion of a compound of formula (I) into a pharmaceutically acceptable salt with a base can be carried out by treatment of such a compound with such a base. One possible method to form such a salt is e.g. by addition of 1/n equivalents of a basic salt such as e.g. M(OH)n, wherein M is metal or ammonium cation and n is number of hydroxide anions, to a solution of the compound in a suitable solvent (e.g. ethanol, ethanol-water mixture, tetrahydrofuran-water mixture) and to remove the solvent by evaporation or lyophilisation.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoroborate (TPTU), or by direct reaction with a suitable alcohol under acidic conditions, as for example in the presence of a strong mineral acid like hydrochloric acid, sulfuric acid and the like. Compounds having a hydroxyl group can be converted to esters with suitable acids by analogous methods.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

As described above, the novel compounds of the present invention have been found to inhibit PDE10A activity. The compounds of the present invention can therefore be used, either alone or in combination with other drugs, for the treatment and/or prophylaxis of diseases which are modulated by PDE10A inhibitors. These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive/compulsive disorders, acute stress disorder or generalized anxiety disorder, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders. Other disorders are diabetes and related disorders, such as type 2 diabetes mellitus, neurodegenerative disorders such as Alzheimer's disease, Huntington's disease, Parkinson's disease, multiple sclerosis, stroke or spinal cord injury, solid tumors and hematological malignancies such as renal cell carcinoma or breast cancer.

The invention therefore also relates to compounds as described above for use as therapeutically active substance.

The invention also relates to pharmaceutical compositions comprising a compound as described above and a therapeutically inert carrier.

In another embodiment, the invention relates to the use of a compound as described above for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

Yet in another embodiment, the invention relates to the use of a compound as described above for the preparation of a medicament for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

The invention also relates to a compound as described above for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

The invention further relates to a compound as described above, when manufactured according to a process as described above.

In another embodiment, the invention relates to a method for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer, which method comprises administering an effective amount of a compound as described above.

Prevention and/or treatment of schizophrenia is a particular indication. Yet particular indication is prevention and/or treatment of positive, negative and/or cognitive symptoms associated with schizophrenia.

The invention further relates to a pharmaceutical composition comprising compounds of formula (I) as defined above and a therapeutically inert carrier.

As described above, the novel compounds of the present invention have been found to inhibit PDE10A activity. The compounds of the present invention can therefore be used, either alone or in combination with other drugs, for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

Yet in another embodiment, the invention relates to the use of a compound of the present invention for the preparation of a medicament for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

The invention also relates to a compound as described above for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

The compounds of formula (I) can have one or more asymmetric C atoms and can therefore exist as an enantiomeric mixture, mixture of stereoisomers or as optically pure compounds. The compounds of formula (I) include all diastereomers, tautomers, racemates and mixtures thereof.

Particular compounds of formula (I) are described in the examples as individual compounds as well as pharmaceutically acceptable salts as well as pharmaceutically acceptable esters thereof. Furthermore, the substituents as found in the specific examples described below, individually constitute particular embodiments of the present invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit PDE10 and to control the cAMP signaling pathway. For example, such amount may be below the amount that is toxic to normal cells, or the mammal as a whole.

In one example, the pharmaceutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, preferably contain from about 25-100 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula (I), or a stereoisomer or pharmaceutically acceptable salt thereof. In a further embodiment includes a pharmaceutical composition comprising a compound of Formula (I), or a stereoisomer or pharmaceutically acceptable salt thereof, together with a pharmaceutically acceptable carrier or excipient.

The following test was carried out in order to determine the activity of the compounds of the present invention. PDE10 activity of the compounds of the present invention was determined using a Scintillation Proximity Assay (SPA)-based method similar to the one previously described (Fawcett, L. et al., Proc Natl Acad Sci USA (2000) 97(7):3702-3707).

The human PDE10A full length assay was performed in 96-well micro titer plates. The reaction mixture of 50 µl contained 20 mM HEPES pH=7.5/10 mM $MgCl_2$/0.05 mg/ml BSA (Sigma cat. # A-7906), 50 nM cGMP (Sigma, cat. # G6129) and 50 nM [$^3$H]-cGMP (GE Healthcare, cat. # TRK392 S.A. 13.2 Ci/mmol), 3.75 ng/well PDE10A enzyme (Enzo Life Science, Lausen, Switzerland cat #SE-534) with or without a specific test compound. A range of concentrations of the potential inhibitor was used to generate data for calculating the concentration of inhibitor resulting in 50% of the effect (e.g. $IC_{50}$, the concentration of the competitor inhibiting PDE10A activity by 50%). Non-specific activity was tested without the enzyme. The reaction was initiated by the addition of the substrate solution (cGMP and [$^3$H]-cGMP) and allowed to progress for 20 minutes at room temperature. The reaction was terminated by adding 25 µl of YSi-SPA scintillation beads (GE Healthcare, cat. # RPNQ0150) in 18 mM zinc sulphate solution (stop reagent). After 1 h under shaking, the plate was centrifuged one minute at 170 g to allow beads to settle. Afterwards, radioactive counts were measured on a Perkin Elmer Top-Count Scintillation plate reader.

The compounds according to formula (I) have an IC50 value below 10 µM, more specifically below 5 µM, yet more specifically below 1 µM. The following table shows data for some examples.

| Example | PDE10A inhibition IC50 [nM] |
| --- | --- |
| 1 | 47.3 |
| 2 | 1.2 |
| 3 | 0.6 |
| 4 | 7.9 |
| 5 | 2.5 |
| 6 | 1.5 |
| 7 | 2.2 |
| 8 | 0.9 |
| 9 | 13.2 |
| 10 | 43.6 |
| 11 | 6.7 |
| 12 | 17.9 |
| 13 | 15.4 |
| 14 | 63.8 |
| 15 | 23.1 |
| 16 | 30.8 |
| 17 | 26.5 |
| 18 | 7.2 |
| 19 | 36.0 |
| 20 | 8.2 |
| 21 | 28.6 |
| 22 | 33.5 |
| 23 | 25.0 |
| 24 | 5.3 |
| 25 | 17 |
| 26 | 21.8 |
| 27 | 3.3 |
| 28 | 3.3 |
| 29 | 9.9 |
| 30 | 19.1 |
| 31 | 2.3 |
| 32 | 2.5 |
| 33 | 0.8 |
| 34 | 1.2 |
| 35 | 1.0 |
| 36 | 1.9 |
| 37 | 3.5 |
| 38 | 29.4 |
| 39 | 23.1 |
| 40 | 17.0 |
| 41 | 3.5 |
| 42 | 7.5 |
| 43 | 4.9 |

Ames Test was performed as a downscaled version of the standard preincubation Ames test and adapted from the method described by Kado et al. with some modifications e.g. Maron. D. M. and B. N. Ames (1983). Revised methods for the Salmonella mutagenicity test. Mutation Research, 113, 173-215. N.Y. Kado, D. Langley and E. Eisenstadt A simple modification of the Salmonella liquid-incubation assay. Increased sensitivity for detecting mutagens in human urine, Mutat Res 121 (1983) 25-32.

The following examples serve to illustrate the present invention in more detail. They are, however, not intended to limit its scope in any manner.

EXAMPLES

Example 1

1-Methyl-5-(2-phenyl-[1,2,4]triazolo[1,5-a]pyridin-6-ylcarbamoyl)-1H-pyrazole-4-carboxylic acid

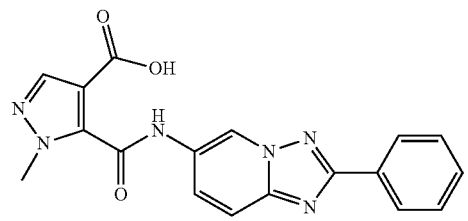 [SMILES: Cn1ncc(C(=O)O)c1C(=O)Nc1ccc2nc(-c3ccccc3)nn2c1]

a) 6-bromo-2-phenyl-[1,2,4]triazolo[1,5-a]pyridine

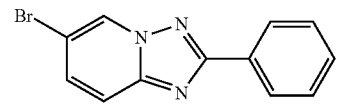

A mixture of 5-bromopyridin-2-amine (2 g, 11.6 mmol), benzonitrile (26.2 g, 26.1 ml, 254 mmol), 1,10-phenanthroline monohydrate (115 mg, 578 μmol) and copper (I) bromide (82.9 mg, 578 μmol) was placed in a 100 ml 2 necked flask. The mixture was heated to 135° C. while air was bubbled gently through the mixture for 2 days. Another portion of copper (I) bromide (82.9 mg, 578 μmol) and 1,10-phenanthroline monohydrate (115 mg, 578 μmol) was added and bubbling and heating was continued for further 8 hours. The solvent was evaporated. Purification by flash chromatography on a 20 g silicagel column using heptane/ethyl acetate 10-50% as eluent and evaporation of the solvents afforded 6-bromo-2-phenyl-[1,2,4]triazolo[1,5-a]pyridine (1.19 g, 38%) as light yellow solid. Mp.: 146° C. MS: m/z=274/276 (M+H$^+$).

b) 2-Phenyl-[1,2,4]triazolo[1,5-a]pyridin-6-yl)-carbamic acid tert-butylester

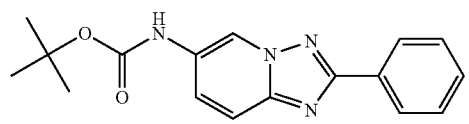 [SMILES: CC(C)(C)OC(=O)Nc1ccc2nc(-c3ccccc3)nn2c1]

A mixture of 6-bromo-2-phenyl-[1,2,4]triazolo[1,5-a]pyridine (1.19 g, 4.34 mmol), tert-butyl carbamate (610 mg, 5.21 mmol) and cesium carbonate (1.98 g, 6.08 mmol) in 1,4-dioxane (30 ml) was purged with argon. Then tris(dibenzylideneacetone)dipalladium(0) (239 mg, 260 μmol) and 4,5-bis(diphenylphosphino)-9,9-dimethylxanthene (301 mg, 521 μmol) were added and the purging was repeated. The mixture was heated to reflux and stirred for 18 hours under argon atmosphere. The reaction mixture was evaporated to dryness and the solid purified by flash chromatography over a 50 g silicagel column using heptane/ethyl acetate 10-50% as eluent. Final evaporation afforded 2-phenyl-[1,2,4]triazolo[1,5-a]pyridin-6-yl)-carbamic acid tert-butylester (1.09 g, 81%) as yellow solid. Mp.: 204° C. MS: m/z=311.3 (M+H+).

c) 2-Phenyl-[1,2,4]triazolo[1,5-a]pyridin-6-ylamine

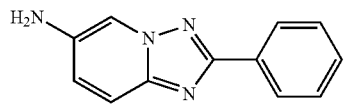

A mixture of 2-phenyl-[1,2,4]triazolo[1,5-a]pyridin-6-yl)-carbamic acid tert-butylester (1.04 g, 3.35 mmol) and hydrochloric acid (5 molar in diethyl ether, 20 ml, 100 mmol) was stirred for 18 hours at 25° C. The solvent was evaporated, the yellow residue was made basic using saturated aqueous sodium hydrogencarbonate and the mixture was extracted with ethyl acetate. The organic layer was washed with brine, dried over magnesium sulfate, filtrated and evaporated to dryness affording 2-phenyl-[1,2,4]triazolo[1,5-a]pyridin-6-ylamine (715 mg, quant.) as yellow solid. Mp.: 201° C. MS: m/z=210.9 (M+H+).

d) 1-Methyl-5-(2-phenyl-[1,2,4]triazolo[1,5-a]pyridin-6-ylcarbamoyl)-1H-pyrazole-4-carboxylic acid ethyl ester

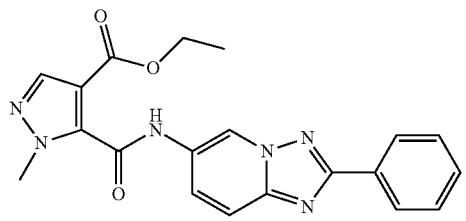

A mixture of 2-phenyl-[1,2,4]triazolo[1,5-a]pyridin-6-ylamine (300 mg, 1.43 mmol), 4-(ethoxycarbonyl)-1-methyl-1H-pyrazole-5-carboxylic acid (339 mg, 1.71 mmol), propylphosphonic anhydride in ethyl acetate 50% (2.27 g, 2.1 ml, 3.57 mmol) and diisopropylethyl amine (553 mg, 748 µl, 4.28 mmol) in tetrahydrofuran (10 ml) was refluxed for 2.5 days. The mixture was evaporated and the residue was treated with saturated aqueous sodiumhydrogen carbonate and stirred for 30 minutes. The solid was filtered off, washed with water and dried, affording 1-methyl-5-(2-phenyl-[1,2,4]triazolo[1,5-a]pyridin-6-ylcarbamoyl)-1H-pyrazole-4-carboxylic acid ethyl ester (483 mg, 87%) as brown solid. Mp.: 251-254° C. MS: m/z=391.1 (M+H+).

e) 1-Methyl-5-(2-phenyl-[1,2,4]triazolo[1,5-a]pyridin-6-ylcarbamoyl)-1H-pyrazole-4-carboxylic acid

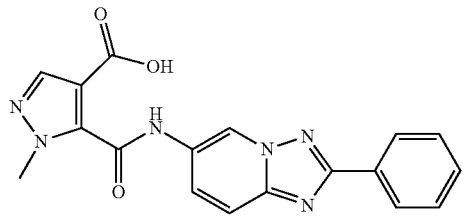

A mixture of ethyl 1-methyl-5-(2-phenyl-[1,2,4]triazolo[1,5-a]pyridin-6-ylcarbamoyl)-1H-pyrazole-4-carboxylate (480 mg, 1.23 mmol) and lithium hydroxide hydrate (155 mg, 3.69 mmol) in methanol (10 ml) and water (3.0 ml) was stirred for 18 hours at 25° C. The solvent was evaporated, the residue was diluted with water and the solution was acidified with hydrochloric acid to pH=0, the precipitated solid was collected, washed with water and dried in vacuo affording 1-methyl-5-(2-phenyl-[1,2,4]triazolo[1,5-a]pyridin-6-ylcarbamoyl)-1H-pyrazole-4-carboxylic acid (435 mg, 98%) as light brown solid. Mp.: 259° C. MS: m/z=361.2 (M−H+).

Example 2

2-Methyl-4-(pyrrolidine-1-carbonyl)-2H-pyrazole-3-carboxylic acid (2-phenyl-[1,2,4]triazolo[1,5-a]pyridin-6-yl)-amide

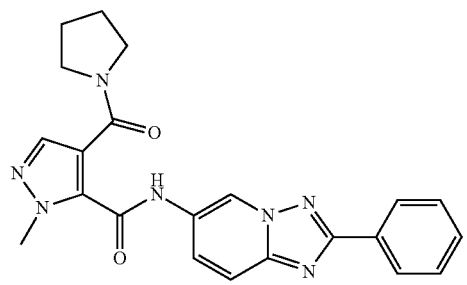 [SMILES: Cn1ncc(C(=O)N2CCCC2)c1C(=O)Nc1ccc2nc(-c3ccccc3)nn2c1]

A mixture of 1-methyl-5-(2-phenyl-[1,2,4]triazolo[1,5-a]pyridin-6-ylcarbamoyl)-1H-pyrazole-4-carboxylic acid (112 mg, 309 µmol), pyrrolidine (220 mg, 256 µl, 3.09 mmol), propylphosphonic anhydride in ethyl acetate 50% (492 mg, 455 µl, 773 µmol) and N,N-diisopropylethylamine (120 mg, 158 µl, 927 µmol) in tetrahydrofuran (7.00 ml) was refluxed for 18 hours. The solvent was evaporated, the residue was triturated with saturated aqueous sodium hydrogencarbonate. The precipitated solid was filtered off, washed with water and dried in vacuo, affording 2-methyl-4-(pyrrolidine-1-carbonyl)-2H-pyrazole-3-carboxylic acid (2-phenyl-[1,2,4]triazolo[1,5-a]pyridin-6-yl)-amide (45 mg, 35%) as brown solid. Mp.: 210° C. MS: m/z=416.1 (M+H+).

Example 3

4-(Azetidine-1-carbonyl)-2-methyl-2H-pyrazole-3-carboxylic acid (2-phenyl-[1,2,4]triazolo[1,5-a]pyridin-6-yl)-amide

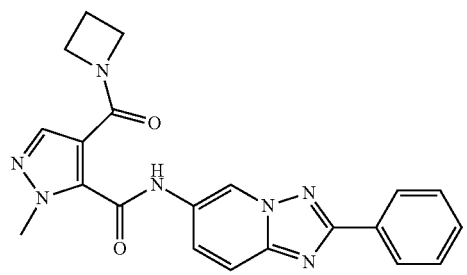 [SMILES: Cn1ncc(C(=O)N2CCC2)c1C(=O)Nc1ccc2nc(-c3ccccc3)nn2c1]

Using azetidine, the title compound was prepared in the same manner as described for example 2. Off-white solid (70 mg, 63.2%). Mp.: 235-236° C. MS: m/z=402.1 (M+H+). Ames test negative.

Example 4

4-(Azetidine-1-carbonyl)-1-methyl-N-(2-(thiazol-4-yl)-[1,2,4]triazolo[1,5-a]pyridin-6-yl)-1H-pyrazole-5-carboxamide

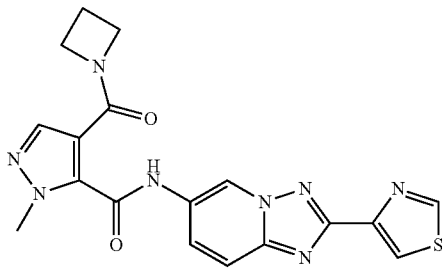 [SMILES: Cn1ncc(C(=O)N2CCC2)c1C(=O)Nc1ccc2nc(-c3cscn3)nn2c1]

Using azetidine and 1-methyl-5-(2-(thiazol-4-yl)-[1,2,4]triazolo[1,5-a]pyridin-6-ylcarbamoyl)-1H-pyrazole-4-carboxylic acid, the title compound was prepared in the same manner as described for example 2. Light brown solid (25 mg, 18%). MS: m/z=409.2 (M+H+).

Example 5

1-Methyl-4-(morpholine-4-carbonyl)-N-(2-phenyl-[1,2,4]triazolo[1,5-a]pyridin-6-yl)-1H-pyrazole-5-carboxamide

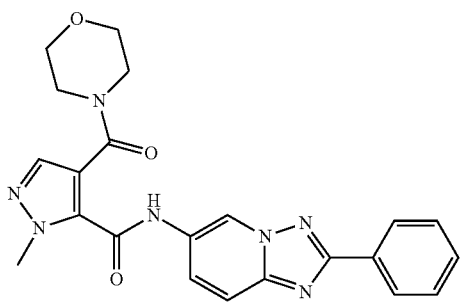 [SMILES: Cn1ncc(C(=O)N2CCOCC2)c1C(=O)Nc1ccc2nc(-c3ccccc3)nn2c1]

Using morpholine, the title compound was prepared in the same manner as described for example 2. Brown solid (106 mg, 80%). Mp.: 183-185° C. MS: m/z=432.5 (M+H+). Ames test negative.

Example 6

4-(3-Fluoro-azetidine-1-carbonyl)-2-methyl-2H-pyrazole-3-carboxylic acid (2-phenyl-[1,2,4]triazolo[1,5-a]pyridin-6-yl)-amide

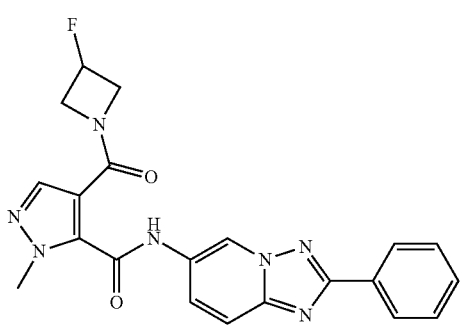 [SMILES: Cn1ncc(C(=O)N2CC(F)C2)c1C(=O)Nc1ccc2nc(-c3ccccc3)nn2c1]

Using 3-fluoroazetidine, the title compound was prepared in the same manner as described for example 2. White solid (83 mg, 64%). Mp.: 243° C. MS: m/z=420.0 (M+H+).

Example 7

2-Methyl-2H-pyrazole-3,4-dicarboxylic acid 4-(ethyl-methyl-amide) 3-[(2-phenyl-[1,2,4]triazolo[1,5-a]pyridin-6-yl)-amide]

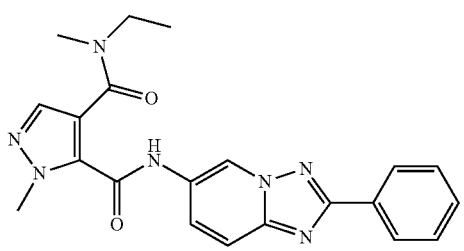 [SMILES: CCN(C)C(=O)c1cnn(C)c1C(=O)Nc1ccc2nc(-c3ccccc3)nn2c1]

Using ethyl-methyl-amine, the title compound was prepared in the same manner as described for example 2. Light yellow solid (63 mg, 57%). MS: m/z=404.1 (M+H+).

Example 8

2-Methyl-2H-pyrazole-3,4-dicarboxylic acid 4-(cyclopropyl-methyl-amide) 3-[(2-phenyl-[1,2,4]triazolo[1,5-a]pyridin-6-yl)-amide]

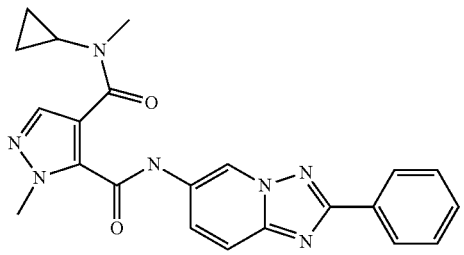 [SMILES: CN(C(=O)c1cnn(C)c1C(=O)Nc1ccc2nc(-c3ccccc3)nn2c1)C1CC1]

Using cyclopropyl-methyl-amine, the title compound was prepared in the same manner as described for example 2. Light yellow solid (63 mg, 57%). Mp.: 106° C. MS: m/z=416.1 (M+H+).

Example 9

2-Methyl-4-(morpholine-4-carbonyl)-2H-pyrazole-3-carboxylic acid (2-pyridin-3-yl-[1,2,4]triazolo[1,5-a]pyridin-6-yl)-amide

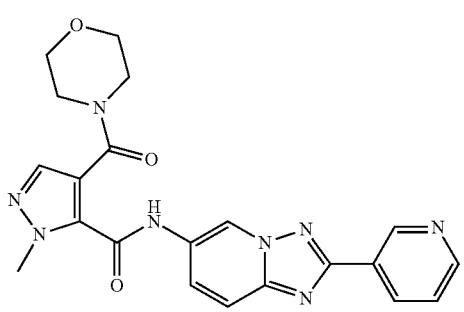 [SMILES: Cn1ncc(C(=O)N2CCOCC2)c1C(=O)Nc1ccc2nc(-c3cccnc3)nn2c1]

a) 6-Bromo-2-pyridin-3-yl-[1,2,4]triazolo[1,5-a]pyridine

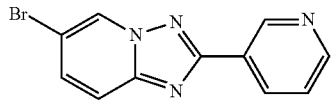 [SMILES: Brc1ccc2nc(-c3cccnc3)nn2c1]

A mixture of 5-bromopyridin-2-amine (2 g, 11.6 mmol), nicotinonitrile (24.1 g, 231 mmol), 1,10-phenanthroline monohydrate (115 mg, 578 μmol) and copper (I) bromide (82.9 mg, 578 μmol) was placed in a 100 ml 2 necked flask and heated to 135° C. Heating was continued while air was bubbled gently through the mixture for 1.5 days. The excess nicotinonitrile was distilled off under reduced pressure and the black residue purified by chromatography (70 g silicagel column using heptane/ethyl acetate 10-100% as eluent). Final evaporation of the solvents afforded 6-bromo-2-pyridin-3-yl-[1,2,4]triazolo[1,5-a]pyridine (1.66 g, 52%) as yellow solid. Mp.: 176° C. MS: m/z=275/277 (M+H+).

b) (2-Pyridin-3-yl-[1,2,4]triazolo[1,5-a]pyridin-6-yl)-carbamic acid tert-butyl ester

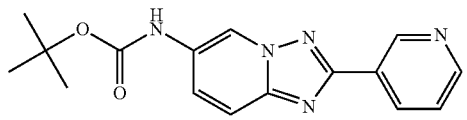 [SMILES: CC(C)(C)OC(=O)Nc1ccc2nc(-c3cccnc3)nn2c1]

A mixture of 6-bromo-2-(pyridin-3-yl)-[1,2,4]triazolo[1,5-a]pyridine (1.65 g, 6.00 mmol), tert-butyl carbamate (843 mg, 7.2 mmol) and cesium carbonate (2.74 g, 8.4 mmol) in 1,4-dioxane (37.8 ml) was purged with argon. Then tris(dibenzylideneacetone)dipalladium(0) (330 mg, 360 μmol) and 4,5-bis(diphenylphosphino)-9,9-dimethylxanthene (416 mg, 720 μmol) were added and the purging was repeated. The mixture was heated to reflux and stirred for 18 hours under argon atmosphere. After evaporation to dryness under reduced pressure, the crude material was purified by flash chromatography (50 g silicagel column using heptane/ethyl acetate 20-100% as eluent). Final evaporation of the solvents afforded (2-pyridin-3-yl-[1,2,4]triazolo[1,5-a]pyridin-6-yl)-carbamic acid tert-butyl ester (1.35 g, 72.5%) as yellow solid. Mp.: 296° C. MS: m/z=312.3 (M+H+).

c) 2-Pyridin-3-yl-[1,2,4]triazolo[1,5-a]pyridin-6-ylamine

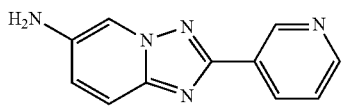

A mixture of tert-butyl 2-(pyridin-3-yl)-[1,2,4]triazolo[1,5-a]pyridin-6-ylcarbamate (1.34 g, 4.3 mmol), dichloromethane (10 ml) and hydrochloric acid (5 molar in diethyl ether (36.0 g, 30 ml, 987 mmol) was stirred for 18 hours at 25° C. The solvents were evaporated under reduced pressure and the residue treated with sodium hydroxide solution (2 molar in water). The mixture was extracted with ethyl acetate, the organic layers were washed with water and brine, dried over magnesium sulfate, filtrated and evaporated to dryness, affording 2-pyridin-3-yl-[1,2,4]triazolo[1,5-a]pyridin-6-ylamine (482 mg, 53%) as light brown solid. Mp.: 230° C. MS: m/z=212.1 (M+H+).

d) 1-Methyl-5-(2-pyridin-3-yl-[1,2,4]triazolo[1,5-a]pyridin-6-ylcarbamoyl)-1H-pyrazole-4-carboxylic acid ethyl ester

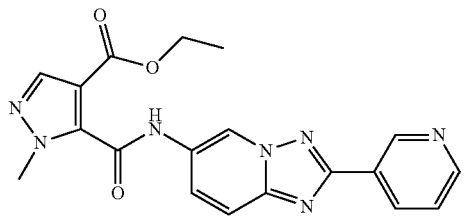 [SMILES: CCOC(=O)c1cnn(C)c1C(=O)Nc1ccc2nc(-c3cccnc3)nn2c1]

A mixture of 2-(pyridin-3-yl)-[1,2,4]triazolo[1,5-a]pyridin-6-ylamine (480 mg, 2.27 mmol), 4-(ethoxycarbonyl)-1-methyl-1H-pyrazole-5-carboxylic acid (495 mg, 2.5 mmol), propylphosphonic anhydride in ethyl acetate 50% (3.62 g, 3.35 ml, 5.68 mmol) and N,N-diisopropylethylamine (1.17 g, 1.55 ml, 9.09 mmol) in tetrahydrofuran (10 ml) was stirred for 18 hours at 70° C. The solvent was evaporated under reduced pressure, the residue was triturated with saturated aqueous sodium hydrogencarbonate. The precipitated solid was filtered off, washed with water and dried in vacuo, affording 1-methyl-5-(2-pyridin-3-yl-[1,2,4]triazolo[1,5-a]pyridin-6-ylcarbamoyl)-1H-pyrazole-4-carboxylic acid ethyl ester (825 mg, 93%) as light brown solid. Mp.: 217° C. MS: m/z=392.1 (M+H+).

e) 1-Methyl-5-(2-pyridin-3-yl-[1,2,4]triazolo[1,5-a]pyridin-6-ylcarbamoyl)-1H-pyrazole-4-carboxylic acid

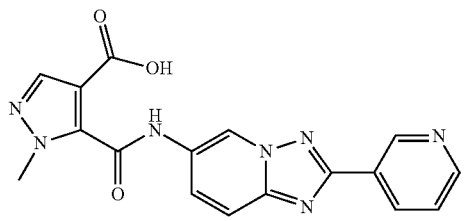 [SMILES: Cn1ncc(C(=O)O)c1C(=O)Nc1ccc2nc(-c3cccnc3)nn2c1]

A mixture of ethyl 1-methyl-5-(2-(pyridin-3-yl)-[1,2,4]triazolo[1,5-a]pyridin-6-ylcarbamoyl)-1H-pyrazole-4-carboxylate (810 mg, 2.07 mmol) and lithium hydroxide hydrate (434 mg, 10.3 mmol) in methanol (30 ml) and water (5 ml) was stirred for 18 hours at 25° C. The mixture was adjusted to pH=7 using hydrochloric acid (2 molar, 5.15 ml) and then evaporated to dryness under reduced pressure. 1-Methyl-5-(2-pyridin-3-yl-[1,2,4]triazolo[1,5-a]pyridin-6-ylcarbamoyl)-1H-pyrazole-4-carboxylic acid (1.38 g) as light brown solid was used without further purification. MS: m/z=364.1 (M+H+).

f) 2-Methyl-4-(morpholine-4-carbonyl)-2H-pyrazole-3-carboxylic acid (2-pyridin-3-yl-[1,2,4]triazolo[1,5-a]pyridin-6-yl)-amide

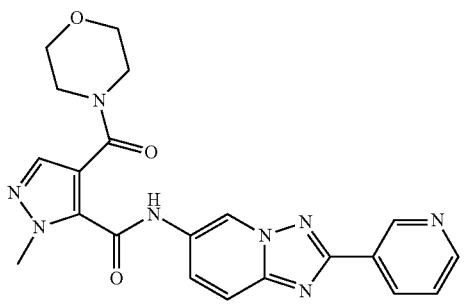 [SMILES: Cn1ncc(C(=O)N2CCOCC2)c1C(=O)Nc1ccc2nc(-c3cccnc3)nn2c1]

Using morpholine and 1-methyl-5-(2-pyridin-3-yl-[1,2,4]triazolo[1,5-a]pyridin-6-ylcarbamoyl)-1H-pyrazole-4-carboxylic acid, the title compound was prepared in the same manner as described for example 2. White solid (53 mg, 32%). Mp.: 229° C. MS: m/z=433.3 (M+H+).

Example 10

4-(Azetidine-1-carbonyl)-1-methyl-N-(2-(pyridin-3-yl)-[1,2,4]triazolo[1,5-a]pyridin-6-yl)-1H-pyrazole-5-carboxamide

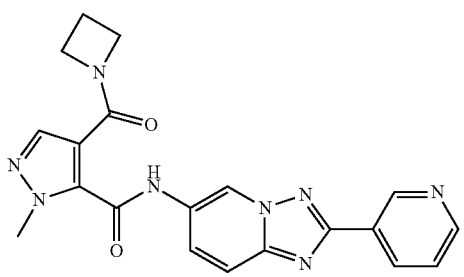 [SMILES: Cn1ncc(C(=O)N2CCC2)c1C(=O)Nc1ccc2nc(-c3cccnc3)nn2c1]

Using azetidine and 1-methyl-5-(2-pyridin-3-yl-[1,2,4]triazolo[1,5-a]pyridin-6-ylcarbamoyl)-1H-pyrazole-4-carboxylic acid, the title compound was prepared in the same manner as described for example 2. White solid (75 mg, 48%). Mp.: 272° C. MS: m/z=403.2 (M+H+).

Example 11

N4-Cyclopropyl-N4,1-dimethyl-N5-(2-(pyridin-3-yl)-[1,2,4]triazolo[1,5-a]pyridin-6-yl)-1H-pyrazole-4,5-dicarboxamide

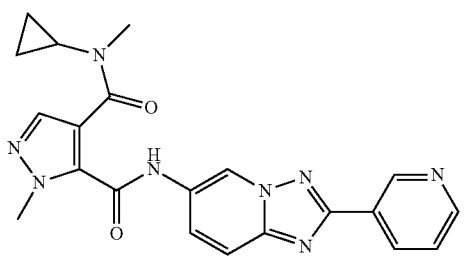 [SMILES: CN(C(=O)c1cnn(C)c1C(=O)Nc1ccc2nc(-c3cccnc3)nn2c1)C1CC1]

Using cyclopropyl-methyl-amine and 1-methyl-5-(2-pyridin-3-yl-[1,2,4]triazolo[1,5-a]pyridin-6-ylcarbamoyl)-1H-pyrazole-4-carboxylic acid, the title compound was prepared in the same manner as described for example 2. White solid (71 mg, 44%). Mp.: 237° C. MS: m/z=417.3 (M+H+). Ames test negative.

Example 12

1-Methyl-N-(2-(pyridin-3-yl)-[1,2,4]triazolo[1,5-a]pyridin-6-yl)-4-(pyrrolidine-1-carbonyl)-1H-pyrazole-5-carboxamide

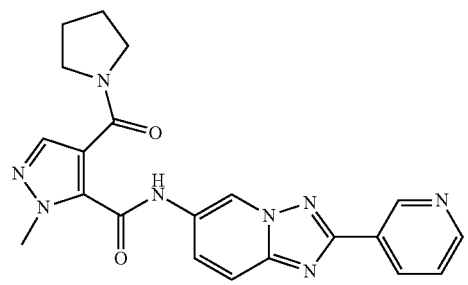 [SMILES: Cn1ncc(C(=O)N2CCCC2)c1C(=O)Nc1ccc2nc(-c3cccnc3)nn2c1]

Using pyrrolidine and 1-methyl-5-(2-pyridin-3-yl-[1,2,4]triazolo[1,5-a]pyridin-6-ylcarbamoyl)-1H-pyrazole-4-carboxylic acid, the title compound was prepared in the same manner as described for example 2. White solid (53 mg, 33%). Mp.: 251° C. MS: m/z=417.3 (M+H+).

Example 13

2-Methyl-4-(pyrrolidine-1-carbonyl)-2H-pyrazole-3-carboxylic acid (2-morpholin-4-yl-[1,2,4]triazolo[1,5-a]pyridin-6-yl)-amide

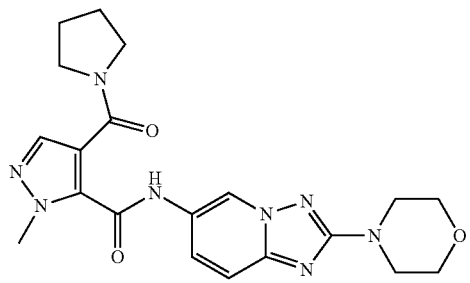 [SMILES: Cn1ncc(C(=O)N2CCCC2)c1C(=O)Nc1ccc2nc(N3CCOCC3)nn2c1]

a) 1-Ethoxycarbonyl-3-(5-bromo-pyridin-2-yl)-thiourea

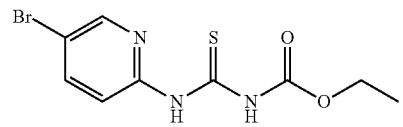 [SMILES: CCOC(=O)NC(=S)Nc1ccc(Br)cn1]

A mixture of 5-bromopyridin-2-amine (14.7 g, 85.0 mmol) and ethoxycarbonyl isothiocyanate (11.1 g, 10.0 ml, 85.0 mmol) in dioxane (300 ml) was stirred for 18 hours at 25° C. under nitrogen atmosphere. The solvent was evaporated under reduced pressure, the solid yellow residue was diluted with ethyl acetate and washed with water and brine, the organic layer was separated, dried over magnesium sulfate, filtrated and evaporated to dryness. 26.2 g (quant.) light yellow solid. Mp.: 159-161° C. MS: m/z=304.0/305.9 (M+H+).

b) 6-Bromo-[1,2,4]triazolo[1,5-a]pyridin-2-ylamine

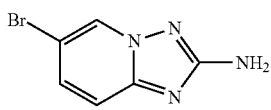

A mixture of hydroxylamine hydrochloride (40.0 g, 575 mmol) and N-ethyldiisopropylamine (44.6 g, 60.3 ml, 345 mmol) in ethanol (734 ml) was stirred for a few minutes at 25° C., then the mixture was added to 1-ethoxycarbonyl-3-(5-bromo-pyridin-2-yl)-thiourea (35 g, 115 mmol) and the resulting mixture was refluxed for 1 day. The solvent was evaporated under reduced pressure and the white solid was treated with 400 ml water. The suspension was stirred for 1 hour, the solid was filtered off, washed with water 3 times and dried under reduced pressure, affording 6-bromo-[1,2,4]triazolo[1,5-a]pyridin-2-ylamine (21 g, 85%) as white solid. Mp.: 185° C. MS: m/z=213.0/215.1 (M+H+).

c) 2,6-Dibromo-[1,2,4]triazolo[1,5-a]pyridine

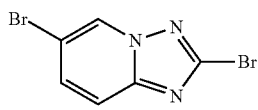

A mixture of 6-bromo-[1,2,4]triazolo[1,5-a]pyridin-2-amine (20.86 g, 97.9 mmol), sodium nitrite (67.6 g, 979 mmol) and benzyltriethylammonium bromide (53.3 g, 196 mmol) in bromoform (1.47 kg, 508 ml, 5.81 mol) was stirred for 30 minutes at 25° C. Then dichloroacetic acid (25.3 g, 16.2 ml, 196 mmol) was added and the mixture was stirred for 20 hours at 25° C. under exclusion of light. 600 ml of water were added to the mixture and stirred for 30 minutes. The mixture was diluted with water and dichloromethane, filtrated over dicalite and the filtrate extracted 3 times with dichloromethane. The organic layers were combined, washed with water, dried over magnesium sulfate, filtrated and evaporated to dryness under reduced pressure. The crude material was purified by flash chromatography in 2 portions over 2×70 g silica columns using dichloromethane/methanol 5% as eluent, affording 2,6-dibromo-[1,2,4]triazolo[1,5-a]pyridine (7 g, 26%) as light brown solid. Mp.: 201° C. MS: m/z=277.7/279.9 (M+H+).

d) 6-Bromo-2-morpholin-4-yl-[1,2,4]triazolo[1,5-a]pyridine

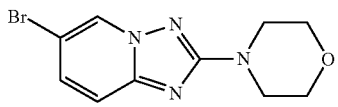 [SMILES: Brc1ccc2nc(N3CCOCC3)nn2c1]

A mixture of 2,6-dibromo-[1,2,4]triazolo[1,5-a]pyridine (1 g, 3.61 mmol) and morpholine (10 g, 10 ml, 115 mmol) was refluxed for 4 hours under argon atmosphere. The mixture was evaporated to dryness under reduced pressure. Flash chromatography (silica gel, 50 g, 30-100% heptane/ethyl acetate) afforded 6-bromo-2-morpholin-4-yl-[1,2,4]triazolo[1,5-a]pyridine (672 mg, 66%) as a light yellow solid. Mp.: 136° C. MS: m/z=283.0/285.0 (M+H+).

e) (2-Morpholin-4-yl-[1,2,4]triazolo[1,5-a]pyridin-6-yl)-carbamic acid tert-butyl ester

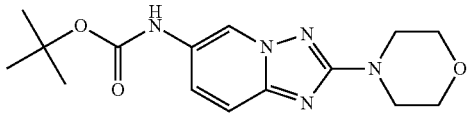 [SMILES: CC(C)(C)OC(=O)Nc1ccc2nc(N3CCOCC3)nn2c1]

A mixture of 4-(6-bromo-[1,2,4]triazolo[1,5-a]pyridin-2-yl)morpholine (200 mg, 706 µmol), tert-butyl carbamate (99.3 mg, 848 µmol) and cesium carbonate (322 mg, 989 µmol) was purged several times with argon, then tris(dibenzylideneacetone)dipalladium(0) (12.9 mg, 14.1 µmol) and 4,5-bis(diphenylphosphino)-9,9-dimethylxanthene (16.3 mg, 28.3 µmol) were added and the mixture was purged with argon again, the vessel was then capped. The resulting mixture was refluxed for 20 hours. The mixture was evaporated to dryness under reduced pressure. Final purification by flash chromatography (20 g silicagel column using heptane/ethyl acetate 70-100 as eluent) afforded (2-morpholin-4-yl-[1,2,4]triazolo[1,5-a]pyridin-6-yl)-carbamic acid tert-butyl ester (46 mg, 20.4%) as yellow solid. Mp.: 166° C. MS: m/z=320.0 (M+H+).

f) 2-Morpholin-4-yl-[1,2,4]triazolo[1,5-a]pyridin-6-ylamine

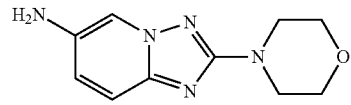 [SMILES: Nc1ccc2nc(N3CCOCC3)nn2c1]

A mixture of tert-butyl 2-morpholin-4-yl-[1,2,4]triazolo[1,5-a]pyridin-6-ylcarbamate (363 mg, 1.14 mmol) and hydrochloric acid (5M in diethyl ether, 24.0 g, 20 ml, 100 mmol) was stirred for 5 hours at 25° C. and then the solvent was evaporated under reduced pressure. The light yellow residue was made alkaline using sodium hydroxide solution (2M in water). The mixture was extracted 2 times with ethyl acetate, the organic layers were combined, washed with water and brine, dried over magnesium sulfate, filtrated and evaporated to dryness, affording 2-morpholin-4-yl-[1,2,4]triazolo[1,5-a]pyridin-6-ylamine (227 mg, 91%) as grey solid. Mp.: 165° C. MS: m/z=220.1 (M+H+).

g) 1-Methyl-5-(2-morpholin-4-yl-[1,2,4]triazolo[1,5-a]pyridin-6-ylcarbamoyl)-1H-pyrazole-4-carboxylic acid ethyl ester

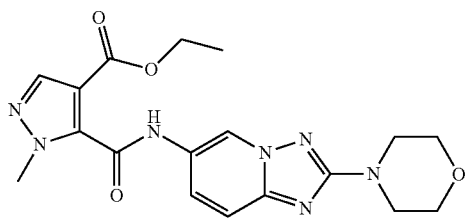 [SMILES: CCOC(=O)c1cnn(C)c1C(=O)Nc1ccc2nc(N3CCOCC3)nn2c1]

A mixture of 2-morpholin-4-yl-[1,2,4]triazolo[1,5-a]pyridin-6-amine (225 mg, 1.03 mmol), 4-(ethoxycarbonyl)-1-methyl-1H-pyrazole-5-carboxylic acid (224 mg, 1.13 mmol), propylphosphonic anhydride in ethyl acetate 50% (1.63 g, 1.51 ml, 2.57 mmol) and N,N-diisopropylethylamine (398 mg, 524 µl, 3.08 mmol) in tetrahydrofuran (7 ml) was refluxed for 18 hours. The solvent was evaporated, the residue was triturated with saturated aqueous sodium hydrogen carbonate. The precipitated solid was filtered off, washed with water and dried in vacuo, affording 1-methyl-5-(2-morpholin-4-yl-[1,2,4]triazolo[1,5-a]pyridin-6-ylcarbamoyl)-1H-pyrazole-4-carboxylic acid ethyl ester (292 mg, 71%) as light brown solid. Mp.: 233.5° C. MS: m/z=400.1 (M+H+).

h) 1-Methyl-5-(2-morpholin-4-yl-[1,2,4]triazolo[1,5-a]pyridin-6-ylcarbamoyl)-1H-pyrazole-4-carboxylic acid

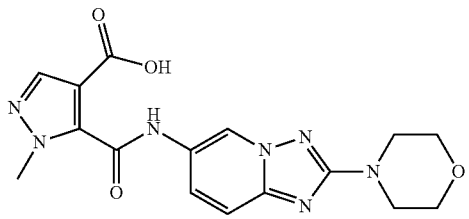 [SMILES: Cn1ncc(C(=O)O)c1C(=O)Nc1ccc2nc(N3CCOCC3)nn2c1]

A mixture of 1-methyl-5-(2-morpholin-4-yl-[1,2,4]triazolo[1,5-a]pyridin-6-ylcarbamoyl)-1H-pyrazole-4-carboxylic acid ethyl ester (282 mg, 0.71 mmol) and lithium hydroxide hydrate (88.9 mg, 2.12 mmol) in methanol (10 ml) and water (3 ml) was stirred for 18 hours at 55° C. The solvents were evaporated under reduced pressure and the residue treated with water (5 ml) and hydrogen chloride (1 molar in water, 2.12 ml). The precipitated solid was filtered off, washed with water and dried under reduced pressure, affording 1-methyl-5-(2-morpholin-4-yl-[1,2,4]triazolo[1,5-a]pyridin-6-ylcarbamoyl)-1H-pyrazole-4-carboxylic acid (187 mg, 71%) as light brown solid. Mp.: 294° C. MS: m/z=372.0 (M+H+).

i) 2-Methyl-4-(pyrrolidine-1-carbonyl)-2H-pyrazole-3-carboxylic acid (2-morpholin-4-yl-[1,2,4]triazolo[1,5-a]pyridin-6-yl)-amide

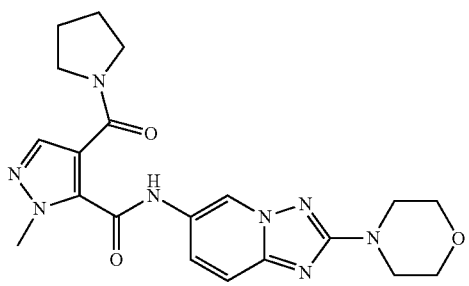 [SMILES: Cn1ncc(C(=O)N2CCCC2)c1C(=O)Nc1ccc2nc(N3CCOCC3)nn2c1]

Using pyrrolidine and 1-methyl-5-(2-morpholin-4-yl-[1,2,4]triazolo[1,5-a]pyridin-6-ylcarbamoyl)-1H-pyrazole-4-carboxylic acid, the title compound was prepared in the same manner as described for example 2. Brown solid (110 mg, 64%). MS: m/z=425 (M+H+).

Example 14

2-Methyl-4-(morpholine-4-carbonyl)-2H-pyrazole-3-carboxylic acid (2-morpholin-4-yl-[1,2,4]triazolo[1,5-a]pyridin-6-yl)-amide

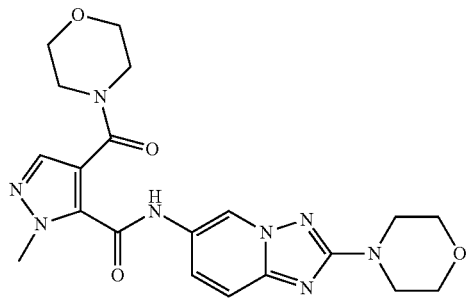 [SMILES: Cn1ncc(C(=O)N2CCOCC2)c1C(=O)Nc1ccc2nc(N3CCOCC3)nn2c1]

Using morpholine and 1-methyl-5-(2-morpholin-4-yl-[1,2,4]triazolo[1,5-a]pyridin-6-ylcarbamoyl)-1H-pyrazole-4-carboxylic acid, the title compound was prepared in the same manner as described for example 2. White solid (130 mg, 65%). MS: m/z=441 (M+H+).

Example 15

2-Methyl-4-(azetidine-4-carbonyl)-2H-pyrazole-3-carboxylic acid (2-morpholin-4-yl-[1,2,4]triazolo[1,5-a]pyridin-6-yl)-amide

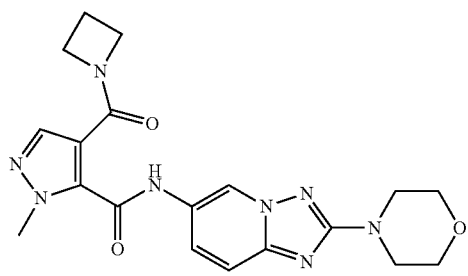 [SMILES: Cn1ncc(C(=O)N2CCC2)c1C(=O)Nc1ccc2nc(N3CCOCC3)nn2c1]

Using azetidine and 1-methyl-5-(2-morpholin-4-yl-[1,2,4]triazolo[1,5-a]pyridin-6-ylcarbamoyl)-1H-pyrazole-4-carboxylic acid, the title compound was prepared in the same manner as described for example 2. Light yellow solid (99 mg, 53%). MS: m/z=411 (M+H+). Ames test negative.

Example 16

2-Methyl-2H-pyrazole-3,4-dicarboxylic acid 4-(ethyl-methyl-amide) 3-[(2-morpholin-4-yl-[1,2,4]triazolo[1,5-a]pyridin-6-yl)-amide]

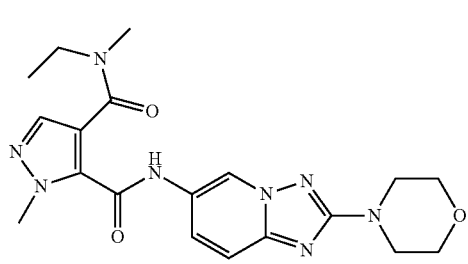 [SMILES: CCN(C)C(=O)c1cnn(C)c1C(=O)Nc1ccc2nc(N3CCOCC3)nn2c1]

Using ethyl-methyl-amine and 1-methyl-5-(2-morpholin-4-yl-[1,2,4]triazolo[1,5-a]pyridin-6-ylcarbamoyl)-1H-pyrazole-4-carboxylic acid, the title compound was prepared in the same manner as described for example 2. White solid (100 mg, 53%). MS: m/z=413 (M+H+).

Example 17

4-(3-Fluoro-azetidine-1-carbonyl)-2-methyl-2H-pyrazole-3-carboxylic acid (2-morpholin-4-yl-[1,2,4]triazolo[1,5-a]pyridin-6-yl)-amide

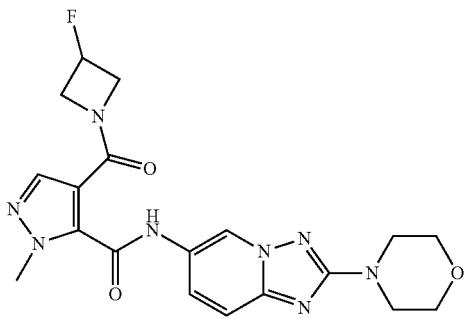 [SMILES: Cn1ncc(C(=O)N2CC(F)C2)c1C(=O)Nc1ccc2nc(N3CCOCC3)nn2c1]

Using 3-fluoro-azetidine and 1-methyl-5-(2-morpholin-4-yl-[1,2,4]triazolo[1,5-a]pyridin-6-ylcarbamoyl)-1H-pyrazole-4-carboxylic acid, the title compound was prepared in the same manner as described for example 2. Off-white solid (150 mg, 76%). MS: m/z=429 (M+H+).

Example 18

2-Methyl-2H-pyrazole-3,4-dicarboxylic acid 4-(cyclopropyl-methyl-amide) 3-[(2-morpholin-4-yl-[1,2,4]triazolo[1,5-a]pyridin-6-yl)-amide]

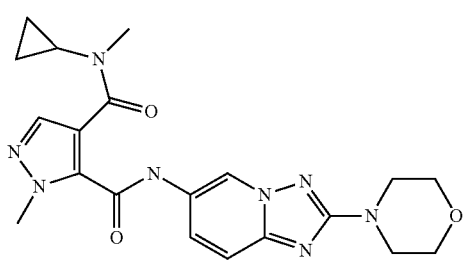 [SMILES: CN(C(=O)c1cnn(C)c1C(=O)Nc1ccc2nc(N3CCOCC3)nn2c1)C1CC1]

Using cyclopropyl-methyl-amine and 1-methyl-5-(2-morpholin-4-yl-[1,2,4]triazolo[1,5-a]pyridin-6-ylcarbamoyl)-1H-pyrazole-4-carboxylic acid, the title compound was prepared in the same manner as described for example 2. Off-white solid (114 mg, 100%). Mp.: 172° C. MS: m/z=425.0 (M+H+).

Example 19

2-Methyl-4-(morpholine-4-carbonyl)-2H-pyrazole-3-carboxylic acid (2-dimethylamino-[1,2,4]triazolo[1,5-a]pyridin-6-yl)-amide

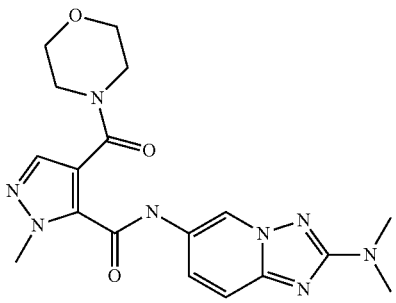 [SMILES: CN(C)c1nc2ccc(NC(=O)c3c(C(=O)N4CCOCC4)cnn3C)cn2n1]

a) (6-Bromo-[1,2,4]triazolo[1,5-a]pyridin-2-yl)-dimethyl-amine

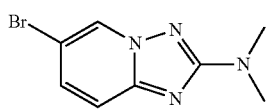

Using dimethylamine, this compound was prepared following the same method as for the synthesis of 6-bromo-2-morpholin-4-yl-[1,2,4]triazolo[1,5-a]pyridine White solid (0.65 g, 75%). MS: m/z=242 (M+H+).

b) (2-Dimethylamino-[1,2,4]triazolo[1,5-a]pyridin-6-yl)-carbamic acid tert-butyl ester

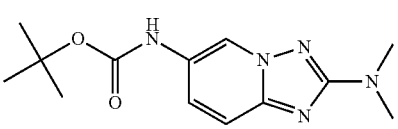 [SMILES: CN(C)c1nc2ccc(NC(=O)OC(C)(C)C)cn2n1]

Using (6-bromo-[1,2,4]triazolo[1,5-a]pyridin-2-yl)-dimethyl-amine, this compound was prepared following the same method as for the synthesis of (2-morpholin-4-yl-[1,2,4]triazolo[1,5-a]pyridin-6-yl)-carbamic acid tert-butyl ester. Reddish yellow solid (250 mg, 33%). MS: m/z=278 (M+H+).

c) N*2*,N*2*-Dimethyl-[1,2,4]triazolo[1,5-a]pyridine-2,6-diamine

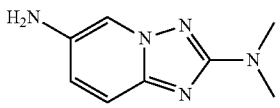

Using (2-dimethylamino-[1,2,4]triazolo[1,5-a]pyridin-6-yl)-carbamic acid tert-butyl ester, this compound was prepared following the same method as for the synthesis of 2-morpholin-4-yl-[1,2,4]triazolo[1,5-a]pyridin-6-ylamine. White solid (64 mg, 83%). MS: m/z=178 (M+H+).

d) 5-(2-Dimethylamino-[1,2,4]triazolo[1,5-a]pyridin-6-ylcarbamoyl)-1-methyl-1H-pyrazole-4-carboxylic acid ethyl ester

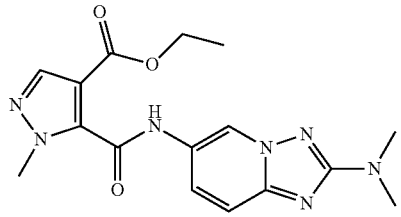 [SMILES: CCOC(=O)c1cnn(C)c1C(=O)Nc1ccc2nc(N(C)C)nn2c1]

Using N*2*,N*2*-dimethyl-[1,2,4]triazolo[1,5-a]pyridine-2,6-diamine, this compound was prepared following the same method as for the synthesis of 1-methyl-5-(2-morpholin-4-yl-[1,2,4]triazolo[1,5-a]pyridin-6-ylcarbamoyl)-1H-pyrazole-4-carboxylic acid ethyl ester. White solid (64 mg, 48%). Mp.: 194° C. MS: m/z=358 (M+H+).

e) 5-(2-Dimethylamino-[1,2,4]triazolo[1,5-a]pyridin-6-ylcarbamoyl)-1-methyl-1H-pyrazole-4-carboxylic acid

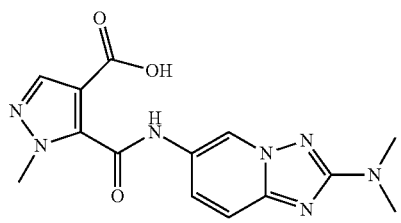 [SMILES: CN(C)c1nc2ccc(NC(=O)c3c(C(=O)O)cnn3C)cn2n1]

Using 5-(2-dimethylamino-[1,2,4]triazolo[1,5-a]pyridin-6-ylcarbamoyl)-1-methyl-1H-pyrazole-4-carboxylic acid ethyl ester, this compound was prepared following the same method as for the synthesis of 1-Methyl-5-(2-morpholino-[1,2,4]triazolo[1,5-a]pyridin-6-ylcarbamoyl)-1H-pyrazole-4-carboxylic acid. Brown solid (41 mg, 70%). MS: m/z=330 (M+H+).

f) 2-Methyl-4-(morpholine-4-carbonyl)-2H-pyrazole-3-carboxylic acid (2-dimethylamino-[1,2,4]triazolo[1,5-a]pyridin-6-yl)-amide

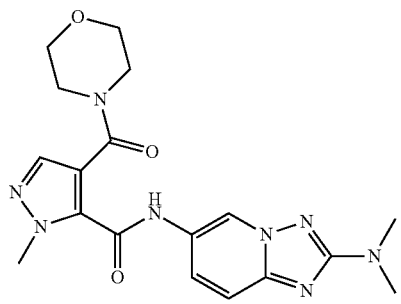 [SMILES: CN(C)c1nc2ccc(NC(=O)c3c(C(=O)N4CCOCC4)cnn3C)cn2n1]

Using morpholine and 5-(2-dimethylamino-[1,2,4]triazolo[1,5-a]pyridin-6-ylcarbamoyl)-1-methyl-1H-pyrazole-4-carboxylic acid, the title compound was prepared in the same manner as described for example 2. Off-white solid (117 mg, 58%). MS: m/z=399 (M+H+). Ames test negative.

Example 20

4-(Azetidine-1-carbonyl)-2-methyl-2H-pyrazole-3-carboxylic acid (2-dimethylamino-[1,2,4]triazolo[1,5-a]pyridin-6-yl)-amide

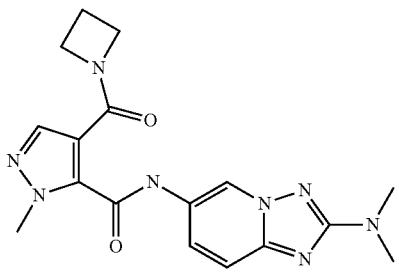 [SMILES: CN(C)c1nc2ccc(NC(=O)c3c(C(=O)N4CCC4)cnn3C)cn2n1]

Using azetidine and 5-(2-dimethylamino-[1,2,4]triazolo[1,5-a]pyridin-6-ylcarbamoyl)-1-methyl-1H-pyrazole-4-carboxylic acid, the title compound was prepared in the same manner as described for example 2. Brown solid (93 mg, 42%). MS: m/z=369 (M+H+). Ames test negative.

Example 21

2-Methyl-4-(pyrrolidine-1-carbonyl)-2H-pyrazole-3-carboxylic acid (2-dimethylamino-[1,2,4]triazolo[1,5-a]pyridin-6-yl)-amide

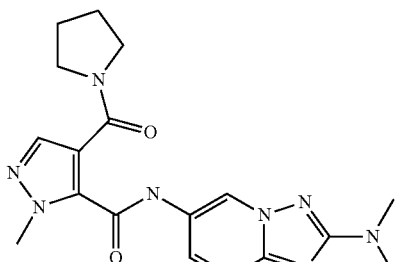

Using pyrrolidine and 5-(2-dimethylamino-[1,2,4]triazolo[1,5-a]pyridin-6-ylcarbamoyl)-1-methyl-1H-pyrazole-4-carboxylic acid, the title compound was prepared in the same manner as described for example 2. Light brown solid (120 mg, 61%). MS: m/z=383 (M+H+).

Example 22

2-Methyl-2H-pyrazole-3,4-dicarboxylic acid 3-[(2-dimethylamino-[1,2,4]triazolo[1,5-a]pyridin-6-yl)-amide]4-(ethyl-methyl-amide)

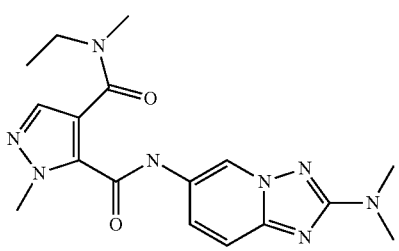 [SMILES: CCN(C)C(=O)c1cnn(C)c1C(=O)Nc1ccc2nc(N(C)C)nn2c1]

Using ethyl-methyl-amine and 5-(2-dimethylamino-[1,2,4]triazolo[1,5-a]pyridin-6-ylcarbamoyl)-1-methyl-1H-pyrazole-4-carboxylic acid, the title compound was prepared in the same manner as described for example 2. Light yellow solid (129 mg, 57%). MS: m/z=371 (M+H+).

Example 23

4-(3-Fluoro-azetidine-1-carbonyl)-2-methyl-2H-pyrazole-3-carboxylic acid (2-dimethylamino-[1,2,4]triazolo[1,5-a]pyridin-6-yl)-amide

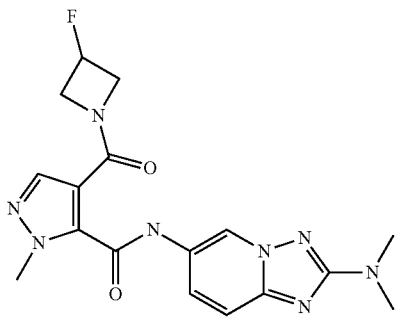 [SMILES: CN(C)c1nc2ccc(NC(=O)c3c(C(=O)N4CC(F)C4)cnn3C)cn2n1]

Using 3-fluoro-azetidine and 5-(2-dimethylamino-[1,2,4]triazolo[1,5-a]pyridin-6-ylcarbamoyl)-1-methyl-1H-pyrazole-4-carboxylic acid, the title compound was prepared in the same manner as described for example 2. Light yellow solid (160 mg, 68%). MS: m/z=387 (M+H+).

Example 24

2-Methyl-2H-pyrazole-3,4-dicarboxylic acid 4-(cyclopropyl-methyl-amide) 3-[(2-dimethylamino-[1,2,4]triazolo[1,5-a]pyridin-6-yl)-amide]

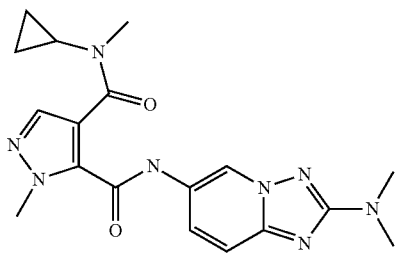 [SMILES: CN(C)c1nc2ccc(NC(=O)c3c(C(=O)N(C)C4CC4)cnn3C)cn2n1]

Using cyclopropyl-methyl-amine and 5-(2-dimethylamino-[1,2,4]triazolo[1,5-a]pyridin-6-ylcarbamoyl)-1-methyl-1H-pyrazole-4-carboxylic acid, the title compound was prepared in the same manner as described for example 2. Light brown oil (30 mg, 49%). MS: m/z=383.0 (M+H+).

Example 25

6-cyclopropyl-3-methoxy-N-(2-phenyl-[1,2,4]triazolo[1,5-a]pyridin-6-yl)pyrazine-2-carboxamide

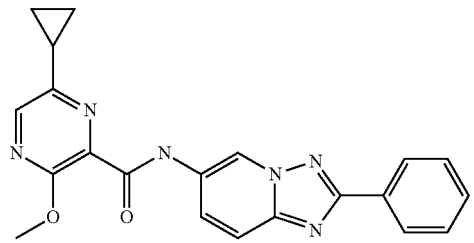 [SMILES: COc1ncc(C2CC2)nc1C(=O)Nc1ccc2nc(-c3ccccc3)nn2c1]

In a 5 ml round bottomed flask 6-cyclopropyl-3-methoxy-pyrazine-2-carboxylic acid (40 mg, 206 µmol), 2-phenyl-[1,2,4]triazolo[1,5-a]pyridin-6-amine (47.6 mg, 227 µmol) and THF (1 ml) were mixed to form a solution. Then propylphosphonic anhydride in ethyl acetate 50% (328 mg, 301 µl, 515 µmol) and N,N-diisopropylethylamine (106 mg, 144 µl, 824 µmol) were added and the mixture heated to 70° C. for 2 hours. The reaction mixture was allowed to cool to room temperature, then 1.5 ml of acetonitrile:water (1:1) was added and the mixture stirred for 10 minutes. The precipitate formed was then filtered off, washed with 1 ml of acetonitrile:water (1:1) and 1 ml acetonitrile, then dried in vacuo to give 6-cyclopropyl-3-methoxy-N-(2-phenyl-[1,2,4]triazolo[1,5-a]pyridin-6-yl)pyrazine-2-carboxamide (45.5 mg, 57.2%) as a yellow solid. MS: m/z=387.2 (M+H+).

Example 26

2-Methyl-4-(morpholine-4-carbonyl)-2H-pyrazole-3-carboxylic acid (2-diethylamino-[1,2,4]triazolo[1,5-a]pyridin-6-yl)-amide

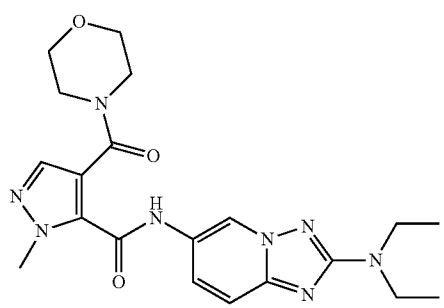 [SMILES: CCN(CC)c1nc2ccc(NC(=O)c3c(C(=O)N4CCOCC4)cnn3C)cn2n1]

a) (6-Bromo-[1,2,4]triazolo[1,5-a]pyridin-2-yl)-diethyl-amine

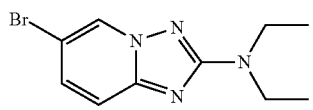

Using diethylamine, this compound was prepared following the same method as for the synthesis of 6-bromo-2-morpholin-4-yl-[1,2,4]triazolo[1,5-a]pyridine Light brown solid (2.0 g, 82%). MS: m/z=270 (M+H+).

b) N*2*,N*2*-Diethyl-[1,2,4]triazolo[1,5-a]pyridine-2,6-diamine

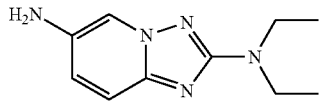

Using (6-bromo-[1,2,4]triazolo[1,5-a]pyridin-2-yl)-diethyl-amine, this compound was prepared following the same methods as for the synthesis of 2-morpholin-4-yl-[1,2,4]triazolo[1,5-a]pyridin-6-ylamine. Brown solid (500 mg, 66%). MS: m/z=206 (M+H+).

c) 5-(2-Diethylamino-[1,2,4]triazolo[1,5-a]pyridin-6-ylcarbamoyl)-1-methyl-1H-pyrazole-4-carboxylic acid ethyl ester

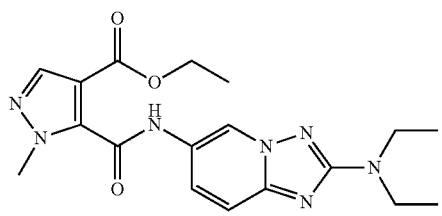 [SMILES: CCOC(=O)c1cnn(C)c1C(=O)Nc1ccc2nc(N(CC)CC)nn2c1]

Using N*2*,N*2*-diethyl-[1,2,4]triazolo[1,5-a]pyridine-2,6-diamine, this compound was prepared following the same method as for the synthesis of 1-methyl-5-(2-morpholin-4-yl-[1,2,4]triazolo[1,5-a]pyridin-6-ylcarbamoyl)-1H-pyrazole-4-carboxylic acid ethyl ester. Off white solid (1.2 g, 45%). MS: m/z=386 (M+H+).

d) 5-(2-Diethylamino-[1,2,4]triazolo[1,5-a]pyridin-6-ylcarbamoyl)-1-methyl-1H-pyrazole-4-carboxylic acid

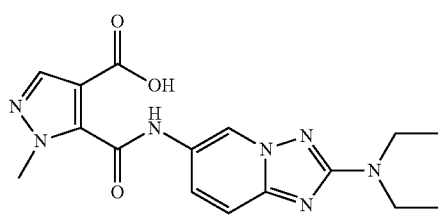 [SMILES: CCN(CC)c1nc2ccc(NC(=O)c3c(C(=O)O)cnn3C)cn2n1]

Using 5-(2-diethylamino-[1,2,4]triazolo[1,5-a]pyridin-6-ylcarbamoyl)-1-methyl-1H-pyrazole-4-carboxylic acid ethyl ester, this compound was prepared following the same method as for the synthesis of 1-Methyl-5-(2-morpholino-[1,2,4]triazolo[1,5-a]pyridin-6-ylcarbamoyl)-1H-pyrazole-4-carboxylic acid. Off white solid (500 mg, 54%). MS: m/z=358 (M+H+).

e) 2-Methyl-4-(morpholine-4-carbonyl)-2H-pyrazole-3-carboxylic acid (2-diethylamino-[1,2,4]triazolo[1,5-a]pyridin-6-yl)-amide

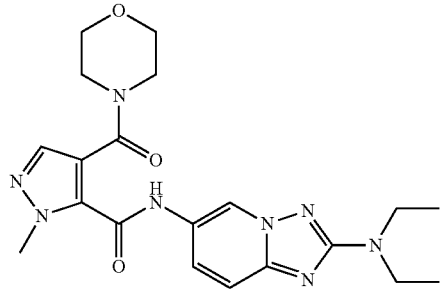 [SMILES: CCN(CC)c1nc2ccc(NC(=O)c3c(C(=O)N4CCOCC4)cnn3C)cn2n1]

Using morpholine and 5-(2-diethylamino-[1,2,4]triazolo[1,5-a]pyridin-6-ylcarbamoyl)-1-methyl-1H-pyrazole-4-carboxylic acid, the title compound was prepared in the same manner as described for example 2. White solid (65 mg, 94%). MS: m/z=357 (M+H+).

Example 27

2-Methyl-4-(pyrrolidine-4-carbonyl)-2H-pyrazole-3-carboxylic acid (2-diethylamino-[1,2,4]triazolo[1,5-a]pyridin-6-yl)-amide

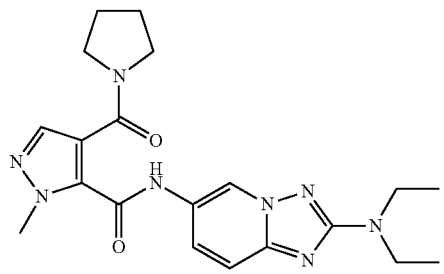 [SMILES: CCN(CC)c1nc2ccc(NC(=O)c3c(C(=O)N4CCCC4)cnn3C)cn2n1]

Using pyrrolidine and 5-(2-diethylamino-[1,2,4]triazolo[1,5-a]pyridin-6-ylcarbamoyl)-1-methyl-1H-pyrazole-4-carboxylic acid, the title compound was prepared in the same manner as described for example 2. White solid (60 mg, 75%). MS: m/z=411 (M+H+).

Example 28

2-Methyl-4-(azetitine-4-carbonyl)-2H-pyrazole-3-carboxylic acid (2-diethylamino-[1,2,4]triazolo[1,5-a]pyridin-6-yl)-amide

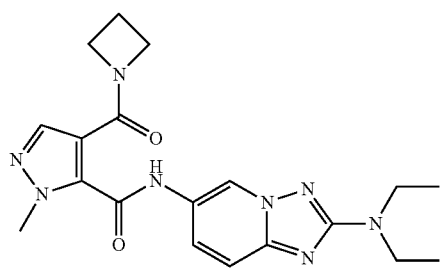 [SMILES: CCN(CC)c1nc2ccc(NC(=O)c3c(C(=O)N4CCC4)cnn3C)cn2n1]

Using azetidine and 5-(2-diethylamino-[1,2,4]triazolo[1,5-a]pyridin-6-ylcarbamoyl)-1-methyl-1H-pyrazole-4-carboxylic acid, the title compound was prepared in the same manner as described for example 2. Off white solid (60 mg, 77%). MS: m/z=397 (M+H+).

Example 29

2-Methyl-2H-pyrazole-3,4-dicarboxylic acid 3-[(2-diethylamino-[1,2,4]triazolo[1,5-a]pyridin-6-yl)-amide]4-(ethyl-methyl-amide)

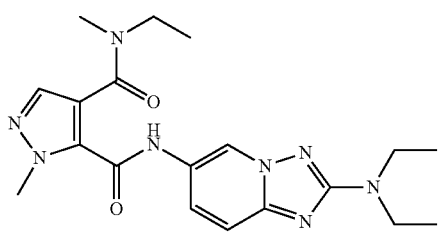 [SMILES: CCN(C)C(=O)c1cnn(C)c1C(=O)Nc1ccc2nc(N(CC)CC)nn2c1]

Using ethyl-methyl-amine and 5-(2-diethylamino-[1,2,4]triazolo[1,5-a]pyridin-6-ylcarbamoyl)-1-methyl-1H-pyrazole-4-carboxylic acid, the title compound was prepared in the same manner as described for example 2. White solid (50 mg, 64%). MS: m/z=399 (M+H+).

Example 30

2-Methyl-2H-pyrazole-3,4-dicarboxylic acid 4-diethylamide 3-[(2-diethylamino-1,2,4]triazolo[1,5-a]pyridin-6-yl)-amide

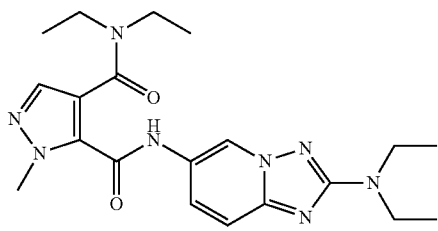 [SMILES: CCN(CC)C(=O)c1cnn(C)c1C(=O)Nc1ccc2nc(N(CC)CC)nn2c1]

Using diethylamine and 5-(2-diethylamino-[1,2,4]triazolo[1,5-a]pyridin-6-ylcarbamoyl)-1-methyl-1H-pyrazole-4-carboxylic acid, the title compound was prepared in the same manner as described for example 2. White solid (70 mg, 87%). MS: m/z=413 (M+H+).

Example 31

2-Methyl-2H-pyrazole-3,4-dicarboxylic acid 4-(cyclopropyl-methyl-amide) 3-[(2-diethylamino-[1,2,4]triazolo[1,5-a]pyridin-6-yl)-amide

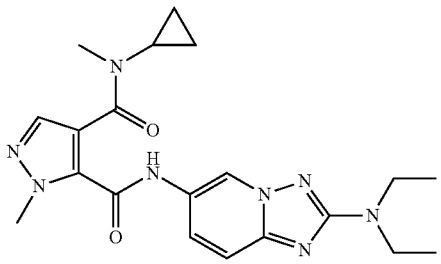 [SMILES: CCN(CC)c1nc2ccc(NC(=O)c3c(C(=O)N(C)C4CC4)cnn3C)cn2n1]

Using cyclopropyl-methyl-amine and 5-(2-diethylamino-[1,2,4]triazolo[1,5-a]pyridin-6-ylcarbamoyl)-1-methyl-1H-pyrazole-4-carboxylic acid, the title compound was prepared in the same manner as described for example 2. White solid (65 mg, 81%). MS: m/z=411 (M+H+).

Example 32

2-Methyl-4-(morpholine-4-carbonyl)-2H-pyrazole-3-carboxylic acid (2-pyrrolidin-1-yl-[1,2,4]triazolo[1,5-a]pyridin-6-yl)-amide

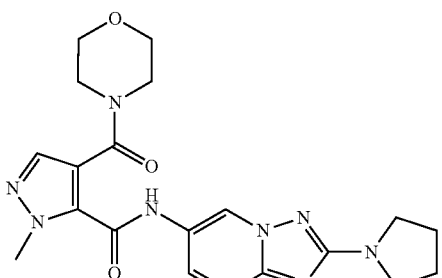

a) 6-Bromo-2-pyrrolidin-1-yl-[1,2,4]triazolo[1,5-a]pyridine

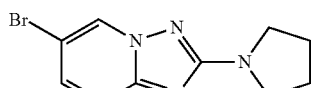

Using pyrrolidine, this compound was prepared following the same method as for the synthesis of 6-bromo-2-morpholin-4-yl-[1,2,4]triazolo[1,5-a]pyridine Off white solid (1.0 g, 41%). MS: m/z=268 (M+H+).

b) 2-Pyrrolidin-1-yl-[1,2,4]triazolo[1,5-a]pyridin-6-ylamine

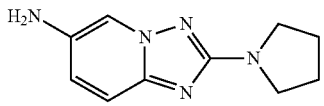 [SMILES: Nc1ccc2nc(N3CCCC3)nn2c1]

Using 6-Bromo-2-pyrrolidin-1-yl-[1,2,4]triazolo[1,5-a]pyridine, this compound was prepared following the same method as for the synthesis of 2-morpholin-4-yl-[1,2,4]triazolo[1,5-a]pyridin-6-ylamine. Brown solid (1.1 g, 81%). MS: m/z=204 (M+H+).

c) 1-Methyl-5-(2-pyrrolidin-1-yl-[1,2,4]triazolo[1,5-a]pyridin-6-ylcarbamoyl)-1H-pyrazole-4-carboxylic acid ethyl ester

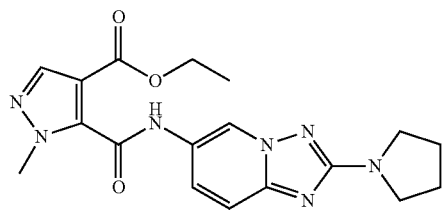 [SMILES: CCOC(=O)c1cnn(C)c1C(=O)Nc1ccc2nc(N3CCCC3)nn2c1]

Using 2-Pyrrolidin-1-yl-[1,2,4]triazolo[1,5-a]pyridin-6-ylamine, this compound was prepared following the same method as for the synthesis of 1-methyl-5-(2-morpholin-4-yl-[1,2,4]triazolo[1,5-a]pyridin-6-ylcarbamoyl)-1H-pyrazole-4-carboxylic acid ethyl ester. Brown solid (1.1 g, 65%). MS: m/z=384 (M+H+).

d) 1-Methyl-5-(2-pyrrolidin-1-yl-[1,2,4]triazolo[1,5-a]pyridin-6-ylcarbamoyl)-1H-pyrazole-4-carboxylic acid

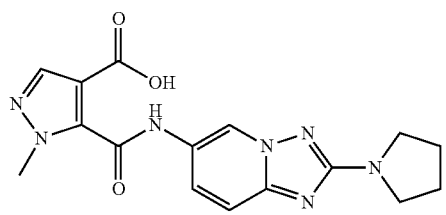 [SMILES: Cn1ncc(C(=O)O)c1C(=O)Nc1ccc2nc(N3CCCC3)nn2c1]

Using 1-Methyl-5-(2-pyrrolidin-1-yl-[1,2,4]triazolo[1,5-a]pyridin-6-ylcarbamoyl)-1H-pyrazole-4-carboxylic acid ethyl ester, this compound was prepared following the same method as for the synthesis of 1-Methyl-5-(2-morpholino-[1,2,4]triazolo[1,5-a]pyridin-6-ylcarbamoyl)-1H-pyrazole-4-carboxylic acid. White solid (430 mg, 93%). MS: m/z=356 (M+H+).

e) 2-Methyl-4-(morpholine-4-carbonyl)-2H-pyrazole-3-carboxylic acid (2-pyrrolidin-1-yl-[1,2,4]triazolo[1,5-a]pyridin-6-yl)-amide

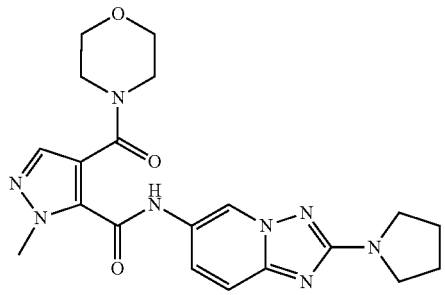 [SMILES: Cn1ncc(C(=O)N2CCOCC2)c1C(=O)Nc1ccc2nc(N3CCCC3)nn2c1]

Using morpholine and 1-Methyl-5-(2-pyrrolidin-1-yl-[1,2,4]triazolo[1,5-a]pyridin-6-ylcarbamoyl)-1H-pyrazole-4-carboxylic acid, the title compound was prepared in the same manner as described for example 2. White solid (68 mg, 95%). MS: m/z=425 (M+H+).

Example 33

4-(Azetidine-1-carbonyl)-2-methyl-2H-pyrazole-3-carboxylic acid (2-pyrrolidin-1-yl-1,2,4]triazolo[1,5-a]pyridin-6-yl)-amide

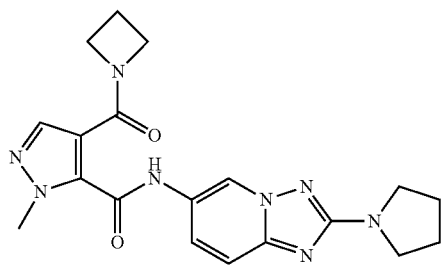 [SMILES: Cn1ncc(C(=O)N2CCC2)c1C(=O)Nc1ccc2nc(N3CCCC3)nn2c1]

Using azetidine and 1-Methyl-5-(2-pyrrolidin-1-yl-[1,2,4]triazolo[1,5-a]pyridin-6-ylcarbamoyl)-1H-pyrazole-4-carboxylic acid, the title compound was prepared in the same manner as described for example 2. White solid (40 mg, 51%). MS: m/z=395 (M+H+).

Example 34

2-Methyl-4-(pyrrolidine-1-carbonyl)-2H-pyrazole-3-carboxylic acid (2-pyrrolidin-1-yl-[1,2,4]triazolo[1,5-a]pyridin-6-yl)-amide

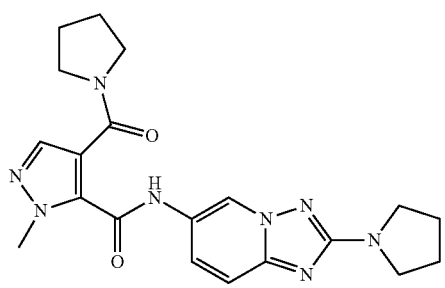 [SMILES: Cn1ncc(C(=O)N2CCCC2)c1C(=O)Nc1ccc2nc(N3CCCC3)nn2c1]

Using pyrrolidine and 1-Methyl-5-(2-pyrrolidin-1-yl-[1,2,4]triazolo[1,5-a]pyridin-6-ylcarbamoyl)-1H-pyrazole-4-carboxylic acid, the title compound was prepared in the same manner as described for example 2. White solid (46 mg, 58%). MS: m/z=409 (M+H+).

Example 35

2-Methyl-2H-pyrazole-3,4-dicarboxylic acid 4-(cyclopropyl-methyl-amide) 3-[(2-pyrrolidin-1-yl-[1,2,4]triazolo[1,5-a]pyridin-6-yl)-amide

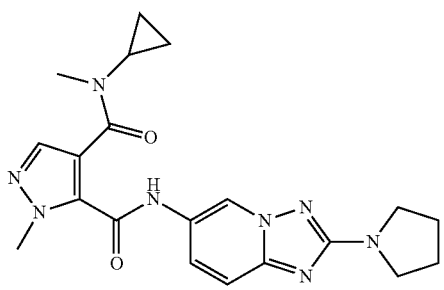 [SMILES: CN(C(=O)c1cnn(C)c1C(=O)Nc1ccc2nc(N3CCCC3)nn2c1)C1CC1]

Using cyclopropyl-methyl-amine and 1-Methyl-5-(2-pyrrolidin-1-yl-[1,2,4]triazolo[1,5-a]pyridin-6-ylcarbamoyl)-1H-pyrazole-4-carboxylic acid, the title compound was prepared in the same manner as described for example 2. White solid (50 mg, 43%). MS: m/z=409 (M+H+).

Example 36

2-Methyl-2H-pyrazole-3,4-dicarboxylic acid 4-(ethyl-methyl-amide) 3-[(2-pyrrolidin-1-yl-[1,2,4]triazolo[1,5-a]pyridin-6-yl)-amide

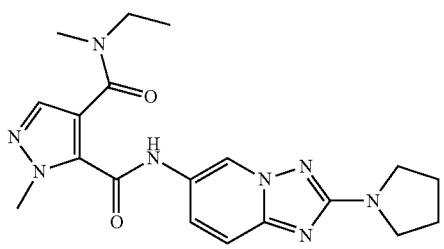 [SMILES: CCN(C)C(=O)c1cnn(C)c1C(=O)Nc1ccc2nc(N3CCCC3)nn2c1]

Using ethyl-methyl-amine and 1-Methyl-5-(2-pyrrolidin-1-yl-[1,2,4]triazolo[1,5-a]pyridin-6-ylcarbamoyl)-1H-pyrazole-4-carboxylic acid, the title compound was prepared in the same manner as described for example 2. White solid (59 mg, 53%). MS: m/z=397 (M+H+).

Example 37

2-Methyl-2H-pyrazole-3,4-dicarboxylic acid 4-diethylamide 3-[(2-pyrrolidin-1-yl-[1,2,4]triazolo[1,5-a]pyridin-6-yl)-amide

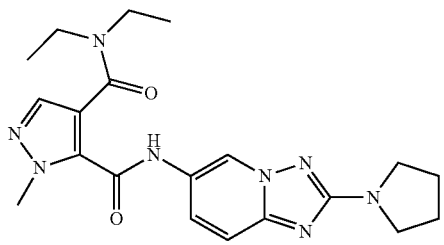 [SMILES: CCN(CC)C(=O)c1cnn(C)c1C(=O)Nc1ccc2nc(N3CCCC3)nn2c1]

Using diethylamine and 1-Methyl-5-(2-pyrrolidin-1-yl-[1,2,4]triazolo[1,5-a]pyridin-6-ylcarbamoyl)-1H-pyrazole-4-carboxylic acid, the title compound was prepared in the same manner as described for example 2. White solid (65 mg, 56%). MS: m/z=411 (M+H+).

Example 38

2-Methyl-2H-pyrazole-3,4-dicarboxylic acid 4-diethylamide 3-{[2-(3-methoxy-pyrrolidin-1-yl)-[1,2,4]triazolo[1,5-a]pyridin-6-yl]-amide

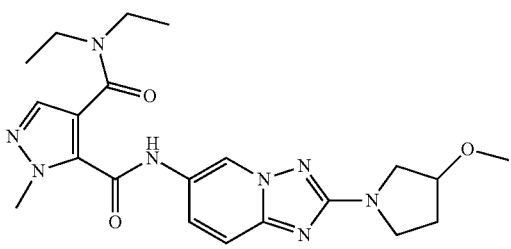 [SMILES: CCN(CC)C(=O)c1cnn(C)c1C(=O)Nc1ccc2nc(N3CCC(OC)C3)nn2c1]

a) 6-Bromo-2-(3-methoxy-pyrrolidin-1-yl)-[1,2,4]triazolo[1,5-a]pyridine

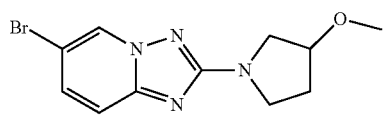 [SMILES: COC1CCN(c2nc3ccc(Br)cn3n2)C1]

Using pyrrolidine, this compound was prepared following the same method as for the synthesis of 6-bromo-2-morpholin-4-yl-[1,2,4]triazolo[1,5-a]pyridine Brown solid (2.5 g, 47%). MS: m/z=298 (M+H+).

b) 2-(3-Methoxy-pyrrolidin-1-yl)-[1,2,4]triazolo[1,5-a]pyridin-6-ylamine

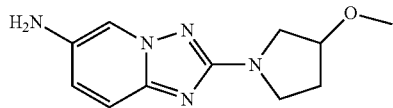 [SMILES: COC1CCN(c2nc3ccc(N)cn3n2)C1]

Using 6-Bromo-2-(3-methoxy-pyrrolidin-1-yl)-[1,2,4]triazolo[1,5-a]pyridine, this compound was prepared following the same method as for the synthesis of 2-morpholin-4-yl-[1,2,4]triazolo[1,5-a]pyridin-6-ylamine. Brown solid (1.4 g, 71%). MS: m/z=234 (M+H+).

c) 5-[2-(3-Methoxy-pyrrolidin-1-yl)-[1,2,4]triazolo[1,5-a]pyridin-6-ylcarbamoyl]-1-methyl-1H-pyrazole-4-carboxylic acid ethyl ester

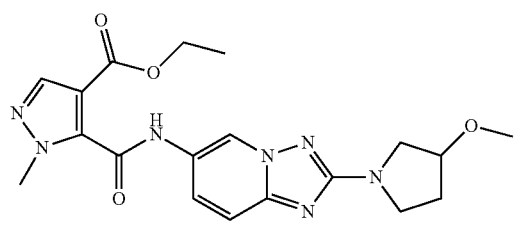 [SMILES: CCOC(=O)c1cnn(C)c1C(=O)Nc1ccc2nc(N3CCC(OC)C3)nn2c1]

Using 2-(3-Methoxy-pyrrolidin-1-yl)-[1,2,4]triazolo[1,5-a]pyridin-6-ylamine, this compound was prepared following the same method as for the synthesis of 1-methyl-5-(2-morpholin-4-yl-[1,2,4]triazolo[1,5-a]pyridin-6-ylcarbamoyl)-1H-pyrazole-4-carboxylic acid ethyl ester. Off white solid (1.2 g, 59%). MS: m/z=414 (M+H+).

d) 5-[2-(3-Methoxy-pyrrolidin-1-yl)-[1,2,4]triazolo[1,5-a]pyridin-6-ylcarbamoyl]-1-methyl-1H-pyrazole-4-carboxylic acid

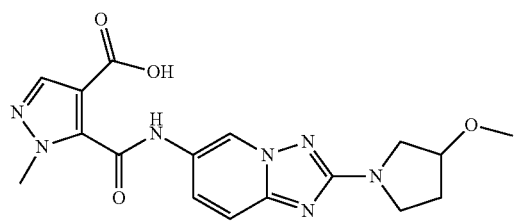 [SMILES: COC1CCN(c2nc3ccc(NC(=O)c4c(C(=O)O)cnn4C)cn3n2)C1]

Using 5-[2-(3-Methoxy-pyrrolidin-1-yl)-[1,2,4]triazolo[1,5-a]pyridin-6-ylcarbamoyl]-1-methyl-1H-pyrazole-4-carboxylic acid ethyl ester, this compound was prepared following the same method as for the synthesis of 1-Methyl-5-(2-morpholino-[1,2,4]triazolo[1,5-a]pyridin-6-ylcarbamoyl)-1H-pyrazole-4-carboxylic acid. Off white solid (690 mg, 82%). MS: m/z=386 (M+H+).

e) 2-Methyl-2H-pyrazole-3,4-dicarboxylic acid 4-diethylamide 3-{[2-(3-methoxy-pyrrolidin-1-yl)-[1,2,4]triazolo[1,5-a]pyridin-6-yl]-amide

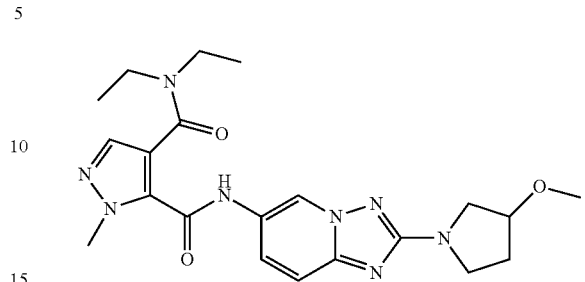

Using diethylamine and 5-[2-(3-Methoxy-pyrrolidin-1-yl)-[1,2,4]triazolo[1,5-a]pyridin-6-ylcarbamoyl]-1-methyl-1H-pyrazole-4-carboxylic acid, the title compound was prepared in the same manner as described for example 2. Off white solid (115 mg, 77%). MS: m/z=441 (M+H+).

Example 39

2-Methyl-4-(morpholine-4-carbonyl)-2H-pyrazole-3-carboxylic acid [2-(3-methoxy-pyrrolidin-1-yl)-[1,2,4]triazolo[1,5-a]pyridin-6-yl]-amide

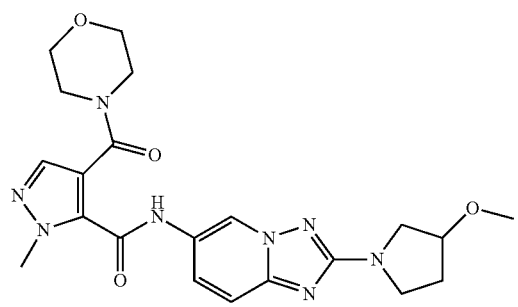 [SMILES: COC1CCN(c2nc3ccc(NC(=O)c4c(C(=O)N5CCOCC5)cnn4C)cn3n2)C1]

Using morpholine and 5-[2-(3-Methoxy-pyrrolidin-1-yl)-[1,2,4]triazolo[1,5-a]pyridin-6-ylcarbamoyl]-1-methyl-1H-pyrazole-4-carboxylic acid, the title compound was prepared in the same manner as described for example 2. Off white solid (42 mg, 51%). MS: m/z=455 (M+H+).

Example 40

2-Methyl-2H-pyrazole-3,4-dicarboxylic acid 4-(ethyl-methyl-amide) 3-{[2-(3-methoxy-pyrrolidin-1-yl)-[1,2,4]triazolo[1,5-a]pyridin-6-yl]-amide}

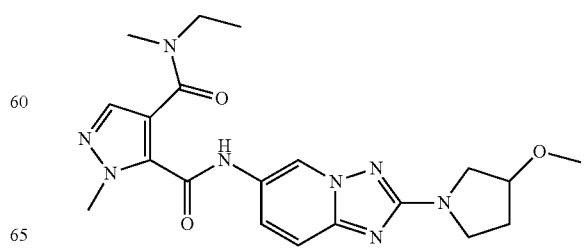

Using ethyl-methyl-amine and 5-[2-(3-Methoxy-pyrrolidin-1-yl)-[1,2,4]triazolo[1,5-a]pyridin-6-ylcarbamoyl]-1-methyl-1H-pyrazole-4-carboxylic acid, the title compound was prepared in the same manner as described for example 2. Off white solid (85 mg, 59%). MS: m/z=427 (M+H+).

Example 41

2-Methyl-2H-pyrazole-3,4-dicarboxylic acid 4-(cyclopropyl-methyl-amide) 3-{[2-(3-methoxy-pyrrolidin-1-yl)-[1,2,4]triazolo[1,5-a]pyridin-6-yl]-amide}

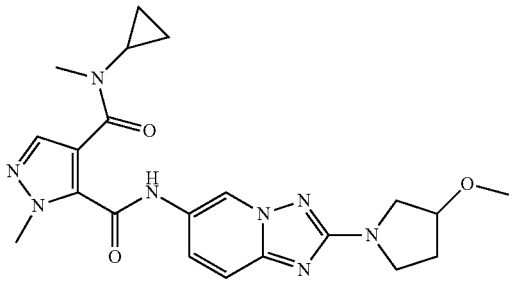 [SMILES: COC1CCN(c2nc3ccc(NC(=O)c4c(C(=O)N(C)C5CC5)cnn4C)cn3n2)C1]

Using cyclopropyl-methyl-amine and 5-[2-(3-Methoxy-pyrrolidin-1-yl)-[1,2,4]triazolo[1,5-a]pyridin-6-ylcarbamoyl]-1-methyl-1H-pyrazole-4-carboxylic acid, the title compound was prepared in the same manner as described for example 2. Off white solid (80 mg, 54%). MS: m/z=439 (M+H+).

Example 42

2-Methyl-4-(pyrrolidine-1-carbonyl)-2H-pyrazole-3-carboxylic acid [2-(3-methoxy-pyrrolidin-1-yl)-[1,2,4]triazolo[1,5-a]pyridin-6-yl]-amide

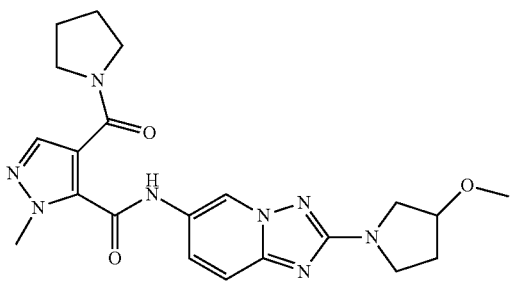 [SMILES: COC1CCN(c2nc3ccc(NC(=O)c4c(C(=O)N5CCCC5)cnn4C)cn3n2)C1]

Using pyrrolidine and 5-[2-(3-Methoxy-pyrrolidin-1-yl)-[1,2,4]triazolo[1,5-a]pyridin-6-ylcarbamoyl]-1-methyl-1H-pyrazole-4-carboxylic acid, the title compound was prepared in the same manner as described for example 2. Off white solid (72 mg, 53%). MS: m/z=439 (M+H+).

Example 43

4-(Azetidine-1-carbonyl)-2-methyl-2H-pyrazole-3-carboxylic acid [2-(3-methoxy-pyrrolidin-1-yl)-[1,2,4]triazolo[1,5-a]pyridin-6-yl]-amide

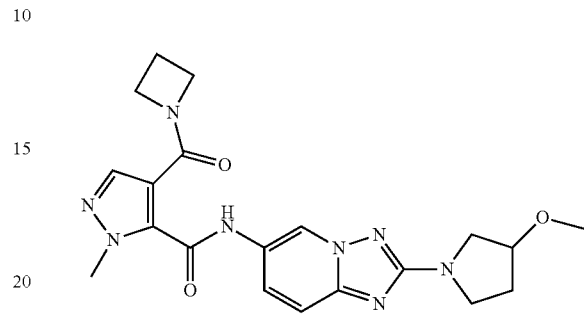

Using azetidine and 5-[2-(3-Methoxy-pyrrolidin-1-yl)-[1,2,4]triazolo[1,5-a]pyridin-6-ylcarbamoyl]-1-methyl-1H-pyrazole-4-carboxylic acid, the title compound was prepared in the same manner as described for example 2. Off white solid (57 mg, 43%). MS: m/z=425 (M+H+).

The invention claimed is:
1. A compound of formula (I)

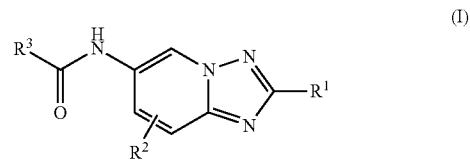

wherein
$R^1$ is aryl, heteroaryl or $NR^4R^5$, wherein said aryl and said heteroaryl can be substituted by 1 to 3 substituents independently selected from the group consisting of hydroxyl, halogen, $C_1$-$C_7$ alkyl, $C_1$-$C_7$ alkoxy and $C_1$-$C_7$ haloalkyl;
$R^2$ is hydrogen, halogen or $C_1$-$C_7$ alkyl;
$R^3$ is aryl or heteroaryl, wherein said aryl and said heteroaryl can be substituted by 1 to 3 substituents independently selected from the group consisting of $C_1$-$C_7$ alkyl, hydroxyl, halogen, —C(O)—$NR^6R^7$ and —C(O)—O—$R^8$;
$R^4$ and $R^5$ are independently $C_1$-$C_7$ alkyl, $C_3$-$C_8$ cycloalkyl, together with the nitrogen atom to which they are attached, form a heterocycloalkyl which can be substituted by 1 to 3 substituents independently selected from the group consisting of hydroxyl, halogen, $C_1$-$C_7$ alkyl, $C_1$-$C_7$ alkoxy and $C_1$-$C_7$ haloalkyl;
$R^6$ and $R^7$, are independently $C_1$-$C_7$ alkyl, $C_3$-$C_8$ cycloalkyl, together with the nitrogen atom to which they are attached, form a heterocycloalkyl which can be substituted by 1 to 3 substituents independently selected from the group consisting of hydroxyl, halogen, $C_1$-$C_7$ alkyl, $C_1$-$C_7$ alkoxy and $C_1$-$C_7$ haloalkyl;
$R^8$ is hydrogen, $C_1$-$C_7$ alkyl, cycloalkyl;
or a pharmaceutically acceptable salt thereof.
2. The compound of claim 1, wherein $R^1$ is phenyl, pyridinyl, thiazolyl or $NR^4R^5$, wherein $R^4$ and $R^5$ are independently selected from C$_1$-C$_3$ alkyl, R$^4$ and R$^5$ together with the nitrogen atom to which they are attached, form a pyrrolidinyl or morpholinyl ring.

3. The compound of claim 1, wherein R$^2$ is hydrogen.

4. The compound of claim 1, wherein R$^3$ is:

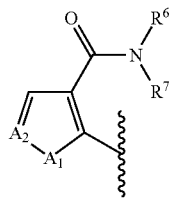

wherein:
A$_1$ is NR$^9$,
A$_2$ is NR$^{9'}$,
R$^6$ and R$^7$ are independently selected from C$_1$-C$_3$ alkyl, C$_3$-C$_8$ cycloalkyl, both optionally substituted by 1 to 3 substituents independently selected from halogen, C$_1$-C$_3$ alkyl, C$_1$-C$_3$ alkoxy and C$_1$-C$_3$ haloalkyl;
R$^6$ and R$^7$ together with the nitrogen atom to which they are attached form a heterocycloalkyl of 4 to 7 ring atoms, comprising 1 or 2 ring heteroatoms selected from N and O, the heterocycloalkyl optionally substituted by 1 to 3 substituents independently selected from halogen, C$_1$-C$_3$ alkyl, C$_1$-C$_3$ alkoxy and C$_1$-C$_3$ haloalkyl, and
R$^9$ and R$^{9'}$ independently selected from hydrogen, C$_1$-C$_3$ alkyl, C$_1$-C$_3$ alkoxy and C$_1$-C$_3$ haloalkyl.

5. The compound of claim 4, wherein:
R$^6$ and R$^7$ are independently selected from C$_1$-C$_3$ alkyl, C$_3$-C$_8$ cycloalkyl,
R$^6$ and R$^7$ together with the nitrogen atom to which they are attached form azetidinyl, pyrrolidinyl and morpholinyl which are optionally substituted by 1 to 3 substituents independently selected from the group consisting of halogen, C$_1$-C$_3$ alkyl, C$_1$-C$_3$ alkoxy and C$_1$-C$_3$ haloalkyl,
R$^9$ is selected from C$_1$-C$_3$ alkyl, C$_1$-C$_3$ alkoxy and C$_1$-C$_3$ haloalkyl, preferably C$_1$-C$_3$ alkyl, and
R$^{9'}$ is selected from hydrogen and C$_1$-C$_3$ alkyl, preferably hydrogen.

6. The compound of claim 1, selected from the group consisting of:
2-Methyl-4-(pyrrolidine-1-carbonyl)-2H-pyrazole-3-carboxylic acid (2-phenyl-[1,2,4]triazolo[1,5-a]pyridin-6-yl)-amide
1-Methyl-5-(2-phenyl-[1,2,4]triazolo[1,5-a]pyridin-6-yl-carbamoyl)-1H-pyrazole-4-carboxylic acid
4-(Azetidine-1-carbonyl)-2-methyl-2H-pyrazole-3-carboxylic acid (2-phenyl-[1,2,4]triazolo[1,5-a]pyridin-6-yl)-amide
4-(Azetidine-1-carbonyl)-1-methyl-N-(2-(thiazol-4-yl)-[1,2,4]triazolo[1,5-a]pyridin-6-yl)-1H-pyrazole-5-carboxamide
1-Methyl-4-(morpholine-4-carbonyl)-N-(2-phenyl-[1,2,4]triazolo[1,5-a]pyridin-6-yl)-1H-pyrazole-5-carboxamide
4-(3-Fluoro-azetidine-1-carbonyl)-2-methyl-2H-pyrazole-3-carboxylic acid (2-phenyl-[1,2,4]triazolo[1,5-a]pyridin-6-yl)-amide
2-Methyl-2H-pyrazole-3,4-dicarboxylic acid 4-(ethyl-methyl-amide) 3-[(2-phenyl-[1,2,4]triazolo[1,5-a]pyridin-6-yl)-amide]
2-Methyl-2H-pyrazole-3,4-dicarboxylic acid 4-(cyclopropyl-methyl-amide) 3-[(2-phenyl-[1,2,4]triazolo[1,5-a]pyridin-6-yl)-amide]
2-Methyl-4-(morpholine-4-carbonyl)-2H-pyrazole-3-carboxylic acid (2-pyridin-3-yl-[1,2,4]triazolo[1,5-a]pyridin-6-yl)-amide
4-(Azetidine-1-carbonyl)-1-methyl-N-(2-(pyridin-3-yl)-[1,2,4]triazolo[1,5-a]pyridin-6-yl)-1H-pyrazole-5-carboxamide
N4-Cyclopropyl-N4,1-dimethyl-N5-(2-(pyridin-3-yl)-[1,2,4]triazolo[1,5-a]pyridin-6-yl)-1H-pyrazole-4,5-dicarboxamide
1-Methyl-N-(2-(pyridin-3-yl)-[1,2,4]triazolo[1,5-a]pyridin-6-yl)-4-(pyrrolidine-1-carbonyl)-1H-pyrazole-5-carboxamide
2-Methyl-4-(pyrrolidine-1-carbonyl)-2H-pyrazole-3-carboxylic acid (2-morpholin-4-yl-[1,2,4]triazolo[1,5-a]pyridin-6-yl)-amide
2-Methyl-4-(morpholine-4-carbonyl)-2H-pyrazole-3-carboxylic acid (2-morpholin-4-yl-[1,2,4]triazolo[1,5-a]pyridin-6-yl)-amide
2-Methyl-4-(azetidine-4-carbonyl)-2H-pyrazole-3-carboxylic acid (2-morpholin-4-yl-[1,2,4]triazolo[1,5-a]pyridin-6-yl)-amide
2-Methyl-2H-pyrazole-3,4-dicarboxylic acid 4-(ethyl-methyl-amide) 3-[(2-morpholin-4-yl-[1,2,4]triazolo[1,5-a]pyridin-6-yl)-amide]
4-(3-Fluoro-azetidine-1-carbonyl)-2-methyl-2H-pyrazole-3-carboxylic acid (2-morpholin-4-yl-[1,2,4]triazolo[1,5-a]pyridin-6-yl)-amide
2-Methyl-2H-pyrazole-3,4-dicarboxylic acid 4-(cyclopropyl-methyl-amide) 3-[(2-morpholin-4-yl-[1,2,4]triazolo[1,5-a]pyridin-6-yl)-amide]
2-Methyl-4-(morpholine-4-carbonyl)-2H-pyrazole-3-carboxylic acid (2-dimethylamino-[1,2,4]triazolo[1,5-a]pyridin-6-yl)-amide
4-(Azetidine-1-carbonyl)-2-methyl-2H-pyrazole-3-carboxylic acid (2-dimethylamino-[1,2,4]triazolo[1,5-a]pyridin-6-yl)-amide
2-Methyl-4-(pyrrolidine-1-carbonyl)-2H-pyrazole-3-carboxylic acid (2-dimethylamino-[1,2,4]triazolo[1,5-a]pyridin-6-yl)-amide
2-Methyl-2H-pyrazole-3,4-dicarboxylic acid 3-[(2-dimethylamino-[1,2,4]triazolo[1,5-a]pyridin-6-yl)-amide]-4-(ethyl-methyl-amide)
4-(3-Fluoro-azetidine-1-carbonyl)-2-methyl-2H-pyrazole-3-carboxylic acid (2-dimethylamino-[1,2,4]triazolo[1,5-a]pyridin-6-yl)-amide
2-Methyl-2H-pyrazole-3,4-dicarboxylic acid 4-(cyclopropyl-methyl-amide) 3-[(2-dimethylamino-[1,2,4]triazolo[1,5-a]pyridin-6-yl)-amide]
6-cyclopropyl-3-methoxy-N-(2-phenyl-[1,2,4]triazolo[1,5-a]pyridin-6-yl)pyrazine-2-carboxamide
2-Methyl-4-(morpholine-4-carbonyl)-2H-pyrazole-3-carboxylic acid (2-diethylamino-[1,2,4]triazolo[1,5-a]pyridin-6-yl)-amide
2-Methyl-4-(pyrrolidine-4-carbonyl)-2H-pyrazole-3-carboxylic acid (2-diethylamino-[1,2,4]triazolo[1,5-a]pyridin-6-yl)-amide
2-Methyl-4-(azetitine-4-carbonyl)-2H-pyrazole-3-carboxylic acid (2-diethylamino-[1,2,4]triazolo[1,5-a]pyridin-6-yl)-amide
2-Methyl-2H-pyrazole-3,4-dicarboxylic acid 3-[(2-diethylamino-[1,2,4]triazolo[1,5-a]pyridin-6-yl)-amide]-4-(ethyl-methyl-amide)

2-Methyl-2H-pyrazole-3,4-dicarboxylic acid 4-diethylamide 3-[(2-diethylamino-1,2,4]triazolo[1,5-a]pyridin-6-yl)-amide 2-Methyl-2H-pyrazole-3,4-dicarboxylic acid 4-(cyclopropyl-methyl-amide) 3-[(2-diethylamino-[1,2,4]triazolo[1,5-a]pyridin-6-yl)-amide 2-Methyl-4-(morpholine-4-carbonyl)-2H-pyrazole-3-carboxylic acid (2-pyrrolidin-1-yl-[1,2,4]triazolo[1,5-a]pyridin-6-yl)-amide 4-(Azetidine-1-carbonyl)-2-methyl-2H-pyrazole-3-carboxylic acid (2-pyrrolidin-1-yl-1,2,4]triazolo[1,5-a]pyridin-6-yl)-amide 2-Methyl-4-(pyrrolidine-1-carbonyl)-2H-pyrazole-3-carboxylic acid (2-pyrrolidin-1-yl-[1,2,4]triazolo[1,5-a]pyridin-6-yl)-amide 2-Methyl-2H-pyrazole-3,4-dicarboxylic acid 4-(cyclopropyl-methyl-amide) 3-[(2-pyrrolidin-1-yl-[1,2,4]triazolo[1,5-a]pyridin-6-yl)-amide 2-Methyl-2H-pyrazole-3,4-dicarboxylic acid 4-(ethyl-methyl-amide) 3-[(2-pyrrolidin-1-yl-[1,2,4]triazolo[1,5-a]pyridin-6-yl)-amide 2-Methyl-2H-pyrazole-3,4-dicarboxylic acid 4-diethylamide 3-[(2-pyrrolidin-1-yl-[1,2,4]triazolo[1,5-a]pyridin-6-yl)-amide 2-Methyl-2H-pyrazole-3,4-dicarboxylic acid 4-diethylamide 3-{[2-(3-methoxy-pyrrolidin-1-yl)-[1,2,4]triazolo[1,5-a]pyridin-6-yl]-amide 2-Methyl-4-(morpholine-4-carbonyl)-2H-pyrazole-3-carboxylic acid [2-(3-methoxy-pyrrolidin-1-yl)-[1,2,4]triazolo[1,5-a]pyridin-6-yl]-amide 2-Methyl-2H-pyrazole-3,4-dicarboxylic acid 4-(ethyl-methyl-amide) 3-{[2-(3-methoxy-pyrrolidin-1-yl)-[1,2,4]triazolo[1,5-a]pyridin-6-yl]-amide}

2-Methyl-2H-pyrazole-3,4-dicarboxylic acid 4-(cyclopropyl-methyl-amide) 3-{[2-(3-methoxy-pyrrolidin-1-yl)-[1,2,4]triazolo[1,5-a]pyridin-6-yl]-amide}

2-Methyl-4-(pyrrolidine-1-carbonyl)-2H-pyrazole-3-carboxylic acid [2-(3-methoxy-pyrrolidin-1-yl)-[1,2,4]triazolo[1,5-a]pyridin-6-yl]-amide 4-(Azetidine-1-carbonyl)-2-methyl-2H-pyrazole-3-carboxylic acid [2-(3-methoxy-pyrrolidin-1-yl)-[1,2,4]triazolo[1,5-a]pyridin-6-yl]-amide.

7. The compound of claim 1, selected from the group consisting of:

4-(Azetidine-1-carbonyl)-2-methyl-2H-pyrazole-3-carboxylic acid (2-phenyl-[1,2,4]triazolo[1,5-a]pyridin-6-yl)-amide 1-Methyl-4-(morpholine-4-carbonyl)-N-(2-phenyl-[1,2,4]triazolo[1,5-a]pyridin-6-yl)-1H-pyrazole-5-carboxamide 4-(3-Fluoro-azetidine-1-carbonyl)-2-methyl-2H-pyrazole-3-carboxylic acid (2-phenyl-[1,2,4]triazolo[1,5-a]pyridin-6-yl)-amide 2-Methyl-4-(morpholine-4-carbonyl)-2H-pyrazole-3-carboxylic acid (2-pyridin-3-yl-[1,2,4]triazolo[1,5-a]pyridin-6-yl)-amide 2-Methyl-4-(pyrrolidine-1-carbonyl)-2H-pyrazole-3-carboxylic acid (2-morpholin-4-yl-[1,2,4]triazolo[1,5-a]pyridin-6-yl)-amide 2-Methyl-2H-pyrazole-3,4-dicarboxylic acid 4-(cyclopropyl-methyl-amide) 3-[(2-morpholin-4-yl-[1,2,4]triazolo[1,5-a]pyridin-6-yl)-amide]

4-(Azetidine-1-carbonyl)-2-methyl-2H-pyrazole-3-carboxylic acid (2-dimethylamino-[1,2,4]triazolo[1,5-a]pyridin-6-yl)-amide 2-Methyl-2H-pyrazole-3,4-dicarboxylic acid 4-(cyclopropyl-methyl-amide) 3-[(2-dimethylamino-[1,2,4]triazolo[1,5-a]pyridin-6-yl)-amide].

8. A pharmaceutical composition comprising a compound in accordance with claim 1 and a therapeutically inert carrier.

9. A process for the manufacture of compounds of formula I as defined in claim 1, which process comprises
a) reacting a compound of formula (2)

(2)

with
b) a compound of formula (3)

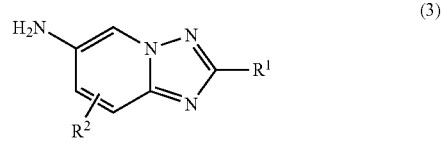

(3)

wherein $R^1$, $R^2$, $R^3$ are as defined above and, if desired, converting the compounds into pharmaceutically acceptable salts thereof.

* * * * *